United States Patent [19]
Vuligonda et al.

[11] Patent Number: 6,034,242
[45] Date of Patent: Mar. 7, 2000

[54] 2,4-PENTADIENOIC ACID DERIVATIVES HAVING RETINOID-LIKE BIOLOGICAL ACTIVITY

[75] Inventors: Vidyasagar Vuligonda, Irvine; Roshantha A. Chandraratna, Mission Viejo, both of Calif.

[73] Assignee: Allergan Sales, Inc., Irvine, Calif.

[21] Appl. No.: 09/165,917

[22] Filed: Oct. 2, 1998

Related U.S. Application Data

[62] Division of application No. 08/854,868, May 12, 1997, Pat. No. 5,817,836, which is a division of application No. 08/656,137, May 31, 1996, Pat. No. 5,663,367, which is a division of application No. 08/466,000, Jun. 6, 1995, Pat. No. 5,675,033.

[51] Int. Cl.[7] ............ C07D 215/06; C07D 215/12
[52] U.S. Cl. ............................. 546/166; 546/165
[58] Field of Search .................... 546/166, 165; 514/311, 314

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 548/237 |
| 4,391,731 | 7/1983 | Boller et al. | 252/299.26 |
| 4,539,154 | 9/1985 | Krebs | 260/410 |
| 4,695,649 | 9/1987 | Magami et al. | 560/86 |
| 4,723,028 | 2/1988 | Shudo | 514/352 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |
| 4,826,969 | 5/1989 | Maignan et al. | 560/100 |
| 4,826,984 | 5/1989 | Berlin et al. | 546/134 |
| 4,855,320 | 8/1989 | Chatterjee et al. | 514/473 |
| 4,895,868 | 1/1990 | Chandraratna | 514/332 |
| 4,923,884 | 5/1990 | Chandraratna | 514/354 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 549/405 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |

(List continued on next page.)

FOREIGN PATENT DOCUMENTS

| | | |
|---|---|---|
| 0098591 | 1/1984 | European Pat. Off. . |
| 0130795 | 1/1985 | European Pat. Off. . |
| 170105 | 2/1986 | European Pat. Off. . |
| 0176032 | 4/1986 | European Pat. Off. . |
| 0176033 | 4/1986 | European Pat. Off. . |
| 0253302 | 1/1988 | European Pat. Off. . |
| 0272921 | 6/1988 | European Pat. Off. . |
| 0284261 | 9/1988 | European Pat. Off. . |

(List continued on next page.)

OTHER PUBLICATIONS

A General Synthesis of Terminal and Internal Arylalkynes by the Palladium–Catalyzed Reaction of Alkynlzinc Reagents with Aryl Halides by Anthony O. King and Ei–i–chi, *J. Org. Chem.*, (1978) 43/2: p. 358.

(List continued on next page.)

*Primary Examiner*—Evelyn Mei Huang
*Attorney, Agent, or Firm*—Gabor L. Szekeres; Robert J. Baran; Martin A. Voet

[57] ABSTRACT

Compounds of Formula 1

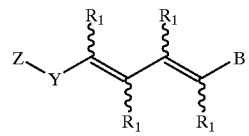

Formula 1 wherein Z is selected from the group consisting of the radicals shown in Formula 3,

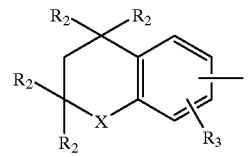

Formula 3

Y is cycloalkyl or cycloalkenyl of 3 to 8 carbons optionally substituted with one or two $R_4$ groups, said groups being optionally substituted with one or two $R_4$ groups, the divalent Y radical being substituted by the Z and $-CR_1=CR_1-CR_1=CR_1$ groups on adjacent carbons; X is $NR_5$; $R_1$ and $R_2$ independently are H, lower alkyl or fluoroalkyl; $R_3$ is hydrogen, lover alkyl, Cl or Br; $R_4$ is lower alkyl, fluoroalkyl or halogen; $R_5$ is H or lower alkyl, and B is hydrogen, COOH or a pharmaceutically acceptable salt thereof, $COOR_8$, $CO_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons, a cycloalkyl group of 5 to 10 carbons or trimethylsilylalkyl where the alkyl group has 1 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, have retinoid like biological activity.

9 Claims, No Drawings

U.S. PATENT DOCUMENTS

| | | | |
|---|---|---|---|
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,354,776 | 10/1994 | Chandratatna | 514/461 |
| 5,380,877 | 1/1995 | Chandraratna | 549/60 |
| 5,391,753 | 2/1995 | Chandraratna | 546/323 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,420,145 | 5/1995 | Shudo | 514/352 |
| 5,426,118 | 6/1995 | Chandraratna | 514/337 |
| 5,434,173 | 7/1995 | Chandraratna | 514/354 |
| 5,451,605 | 9/1995 | Chandraratna et al. | 514/475 |
| 5,455,265 | 10/1995 | Chandraratna | 514/448 |
| 5,466,861 | 11/1995 | Dawson et al. | 560/100 |
| 5,468,879 | 11/1995 | Chandraratna | 549/23 |
| 5,470,999 | 11/1995 | Chandraratna | 560/100 |
| 5,475,022 | 12/1995 | Chandraratna | 514/448 |
| 5,475,113 | 12/1995 | Chandraratna | 548/203 |
| 5,489,584 | 2/1996 | Vuligonda et al. | 514/188 |
| 5,498,755 | 3/1996 | Chandraratna et al. | 564/272 |
| 5,498,795 | 3/1996 | Song et al. | 562/474 |
| 5,514,825 | 5/1996 | Vuligonda et al. | 558/462 |
| 5,516,904 | 5/1996 | Chandraratna | 514/269 |
| 5,523,457 | 6/1996 | Starrett, Jr. et al. | 560/24 |
| 5,534,516 | 7/1996 | Chandraratna | 514/253 |
| 5,534,641 | 7/1996 | Song et al. | 549/416 |
| 5,543,534 | 8/1996 | Vuligonda et al. | 549/421 |
| 5,556,996 | 9/1996 | Beard et al. | 549/407 |
| 5,559,248 | 9/1996 | Starrett, Jr. et al. | 549/79 |
| 5,563,292 | 10/1996 | Sheh et al. | 560/255 |
| 5,591,858 | 1/1997 | Vuligonda et al. | 546/322 |
| 5,599,819 | 2/1997 | Chandraratna | 514/314 |
| 5,599,967 | 2/1997 | Vuligonda et al. | 560/48 |
| 5,602,130 | 2/1997 | Chandraratna | 514/247 |
| 5,602,135 | 2/1997 | Chandraratna | 514/252 |
| 5,605,915 | 2/1997 | Vuligond et al. | 514/356 |
| 5,616,597 | 4/1997 | Chandraratna | 514/365 |
| 5,616,712 | 4/1997 | Teng et al. | 546/158 |
| 5,618,836 | 4/1997 | Chandraratna | 514/444 |
| 5,618,931 | 4/1997 | Beard et al. | 544/224 |
| 5,618,943 | 4/1997 | Vuligonda et al. | 546/342 |
| 5,648,503 | 7/1997 | Vuligonda et al. | 549/13 |
| 5,648,514 | 7/1997 | Johnson et al. | 560/102 |
| 5,654,469 | 8/1997 | Vuligonda et al. | 560/56 |
| 5,663,347 | 9/1997 | Chandraratna | 546/152 |
| 5,663,357 | 9/1997 | Teng et al. | 546/323 |
| 5,663,367 | 9/1997 | Vuligonda et al. | 549/4 |
| 5,672,710 | 9/1997 | Beard et al. | 548/188 |
| 5,675,024 | 10/1997 | Teng et al. | 549/405 |
| 5,675,033 | 10/1997 | Vuligonda et al. | 560/100 |
| 5,677,320 | 10/1997 | Chandraratna | 514/362 |
| 5,677,323 | 10/1997 | Chandraratna | 514/374 |
| 5,677,451 | 10/1997 | Chandraratna | 544/238 |
| 5,817,836 | 10/1998 | Vuligonda et al. | 549/23 |

FOREIGN PATENT DOCUMENTS

| | | |
|---|---|---|
| 0284288 | 9/1988 | European Pat. Off. . |
| 0286364 | 10/1988 | European Pat. Off. . |
| 0303186 | 2/1989 | European Pat. Off. . |
| 0303915 | 2/1989 | European Pat. Off. . |
| 176034 | 4/1989 | European Pat. Off. . |
| 0315071 | 5/1989 | European Pat. Off. . |
| 0350846 | 7/1989 | European Pat. Off. . |
| 0412387 | 2/1991 | European Pat. Off. . |
| 0478787 | 10/1991 | European Pat. Off. . |
| 0514269 | 11/1992 | European Pat. Off. . |
| 0617020 | 9/1994 | European Pat. Off. . |
| 0619116 | 10/1994 | European Pat. Off. . |
| 0661259 | 5/1995 | European Pat. Off. . |
| 0661258 | 7/1995 | European Pat. Off. . |
| 0661261 | 7/1995 | European Pat. Off. . |
| 718285 | 6/1996 | European Pat. Off. . |
| 0718285 | 8/1996 | European Pat. Off. . |
| 3316932 | 11/1983 | Germany . |
| 3524199 | 1/1986 | Germany . |
| 3602473 | 7/1987 | Germany . |
| 3708060 | 9/1987 | Germany . |
| 3715955 | 11/1987 | Germany . |
| 2190378 | 11/1987 | United Kingdom . |
| 85/00806 | 2/1985 | WIPO . |
| 85/04652 | 10/1985 | WIPO . |
| 91/16051 | 10/1991 | WIPO . |
| 92/06948 | 4/1992 | WIPO . |
| 93/03713 | 3/1993 | WIPO . |
| 93/11755 | 6/1993 | WIPO . |
| 93/21146 | 10/1993 | WIPO . |
| 94/14777 | 7/1994 | WIPO . |
| 95/04036 | 2/1995 | WIPO . |
| 96/05165 | 2/1996 | WIPO . |

OTHER PUBLICATIONS

Conversion of Methyl Ketones into Terminal Acetylenes and (E)–Tri–substituted Olefins of Terpenoid Origin by Ei–ichi, et al., *J. Org. Chem.,* (1980) 45/12: p. 2526.

Sporn et al. in *J. Amer. Acad. Derm..,* (1986) 15:756–764.

"A Convenient Synthesis of Ethynylarenes and Diethynylarenes" by S. Takahashi et al. *Synthesis* (1980) p. 627–630.

Shudo et al. in *Chem. Phar. Bull.,* (1985) 33:404–407.

Kagechika et al. in *J. Med. Chem.,* (1988) 31:2182–2192.

Chemistry and Biology of Synthetic Retinoids by Marcia I. Dawson and William H. Okamura, published by CRC Press, Inc., 1990, p. 334–335, 354.

Synthesis of 2,2'–Diacyl–1,1'–Biaryls. Regiocontrolled Protection of . . . by Mervic, et al, *J. Org. Chem.,* (1980) No. 45, p. 4720–4725.

A Dopamine Receptor Model and Its Application in the Design of a New Class of Rigid Pyrrolo[2,3–g]isoquinoline Antipsychotics, Gary L. Olson et al. *American Chemical Societe,* (1981) 24/9:1026–1031.

6.2.3 Conformational Restriction, Williams, et al., *Drug Discovery and Development,* The Humana Press, (1987) pp. 54–55.

V. Retinoid Structure–Biological Activity Relationships, Chemistry and Biology of Synthetic Retinoids, (1990) pp. 324–356.

Davis et al. *J. Organomettalic Chem* (1990) 387:381–390.

"Effects of 13–Cis–Retinoic Acid, All Trans–Retinoic Acid and Acitretin on the Proliferation, Lipid Synthesis and Keratin Expression of Cultured Human Sebocytes in Vitro" C.C. Zouboulis, *the Journal of Investigative Dermatology*, (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology*, (1991) 96/3:.

"Synthesis and Evaluation of Stilbene and Dihydrostilbene Derivateives as Potential Anticancer Agents That Inhibit Tubulin Polymerization" by Cushman, Mark et al. *J. Med. Chem.*, (1991), 34:2579–2588.

"Synthesis and Evaluationof New Pretoein Tyrosine Kinase Inhibitors. Part 1. Pyridine–Containing Stilbenes and Amides" by Cushman, Mark et al. *Bioorganic & Medicinal Chemistry Letters,* (1991) 1/4:211–214.

"Di– and Tri–methoxystyryl Derivatives of Heterocyclic Nitrogen Compounds" by Bahner,C. T. et al. *Arzneim–Forsch./Drug Res.* (1981)31 (I), Nr. 3.

"Retinobenzoic acids. 3. Structure–Activity Relationships of Retinoidal Azobenzene–4–Carboxylic Acids and Stilbene–4– Carboxylic Acids" by H. Kagechika et al., *Journal of Medicinal Chemistry,* (1989), 32:1098–1108.

Eyrolles, L. et al. "Retinoid Antagonists: Molecular Design Based on the Ligand Superfamily Concept" *Med. Chem. Res.,* (1992) 2:361–367.

Liu, S. S. et al. "Systemic Pharmacokinetics of Acetylenic Retinoids in Rats", *Drug Metabolism and Disposition,* (1990) 18/6: 1071–1077.

Chemical Abstracts, vol. 122, No. 13, Mar. 27, 1995 abstract No. 151372m, (S. Kaku et al.).

Chemical Abstracts, vol. 117, No. 13, Sep. 28, 1992 abstract No. 124091j, (S. Sun et al.).

European Journal of Biochemistry, vol. 212, No. 1, 1993, Berlin, pp. 13–26, XP000618300 (S. Keidel et al.).

Journal of Medicinal Chemistry, vol. 39, No. 16, Aug. 2, 1996, pp. 3035–3038, Min Teng et al.

Journal of Medicinal Chemistry, vol. 37, No. 10, May 13, 1994, pp. 1508–1517, Laurence Eyrolles.

Biochemical and Biophysical Research Communications, vol. 155 No. 1, 1988, pp. 503–508.

Chemical Abstracts, vol. 121, No. 9, 1994.

Database WPI, Section CH, Week 9416, Derwent Publications Ltd. London, GB; Class B05, AN 94–128759 and JP 6078266A, see English language abstract in Derwent.

Journal of Medicinal Chemistry, vol. 38, No. 16, Aug. 4, 1995, pp. 3163–73.

Jones et al., "A dose–response study of 13–cis–retinoic acid in acne vulgaris", *British Journal of Dermatology,* (1983) 108, 333–343.

Fekrat, et al., "The Effect of Oral 13–cis–retinoic Acid on Retinal Redetachment after Surgical Repair in Eyes with Proliferative Vitreoretinopathy", *Ophthalmology,* vol. 102, No. 3, (Mar. 1995), pp. 412–418.

Nagpal, et al. "Separation of Transactivation and AP1 Antagonism Functions of Retinoic Acid Receptor $\alpha^*$", *The Journal of Biological Chemistry,* 270/2(1995): 923–927.

Allegretto, et al., "Transactivation Properties of Retinoic Acid and Retinoid X Receptors in Mammalian Cells and Yeast", *The Journal of Biological Chemistry,* vol. 268, No. 35 (Dec. 15, 1993), pp. 26625–26633.

Gruapner, et al., "6'–Substituted Naphthalene–2–Carboxylic Acid Analogs, A New Class of Retinoic Acid Receptor Subtype–Specific Ligands," *Biochemical and Biophysical Communications,* vol. 179, No. 3 (Sep. 30, 1991), pp. 1554–1561.

Moore, et al., "Retinoic Acid and Interferon in Human Cancer: Mechanistic and Clinical Studies," *Seminars in Hematology,* 31/4, Suppl 5 (Oct. 1994), pp. 31–37.

2,4-PENTADIENOIC ACID DERIVATIVES HAVING RETINOID-LIKE BIOLOGICAL ACTIVITY

CROSS-REFERENCE TO RELATED APPLICATION

This application is a divisional of pending application Ser. No. 08/854,868 filed on May 12, 1997, to be issued as U.S. Pat. No. 5,817,836, which is a divisional of application Ser. No. 08/656,137, filed on May 31, 1996, now issued as U.S. Pat. No. 5,663,367, which is a divisional of application Ser. No. 08/466,000, filed on Jun. 6, 1995, now issued as U.S. Pat. No. 5,675,033.

FIELD OF THE INVENTION

The present invention relates to novel compounds having retinoid-like activity. More specifically, the present invention relates to compounds having a 2,4-pentadienoic acid or 2,4-pentadienoic acid ester function which is substituted in the 5-position with a tetrahydronaphthyl-aryl, chromanyl-aryl, thiochromanyl-aryl, 1,2,3,4-tetrahydroquinolinyl-aryl or with a tetrahydronaphthyl-cycloalkyl, chromanyl-cycloalkyl, thiochromanyl-cycloalkyl, 1,2,3,4-tetrahydroquinolinyl-cycloalkyl group. The acid function may also be converted to an alcohol, aldehyde or ketone or derivatives thereof, or may be reduced to —$CH_3$, and the tetrahydronaphthyl-aryl, chromanyl-aryl, thiochromanyl-aryl, 1,2,3,4-tetrahydroquinolinyl-aryl, tetrahydronaphthyl-cycloalkyl, chromanyl-cycloalkyl, thiochromanyl-cycloalkyl, and 1,2,3,4-tetrahydroquinolinyl-cycloalkyl groups may be further substituted with one or more alkyl substituents.

BACKGROUND ART

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

U.S. Pat. Nos. 4,740,519 (Shroot et al.), 4,826,969 (Maignan et al.), 4,326,055 (Loeliger et al.), 5,130,335 (Chandraratna et al.), 5,037,825 (Klaus et al.), 5,231,113 (Chandraratna et al.), 5,324,840 (Chandraratna), Published European Patent Application Nos. 0 176 034 A (Wuest et al.), 0 350 846 A (Klaus et al.), 0 176 032 A (Frickel et al.), 0 176 033 A (Frickel et al.), 0 253 302 A (Klaus et al.), 0 303 915 A (Bryce et al.), UK Patent Application GB 2190378 A (Klaus et al.), German Patent Application Nos. DE 3715955 Al (Klaus et al.), DE 3602473 A1 (Wuest et al., and the articles J. Amer. Acad. Derm. 15: 756–764 (1986) (Sporn et al.), Chem. Pharm. Bull. 33: 404–407 (1985) (Shudo et al.), J. Med Chem. 1988 31, 2182–2192 (Kagechika et al.), Chemistry and Biology of Synthetic Retinoids CRC Press Inc. 1990 p 334–335, 354 (Dawson et al.), describe or relate to compounds which include a tetrahydronaphthyl moiety and have retinoid-like or related biological activity.

U.S. Pat. Nos. 5,278,318, 5,324,840, 5,324,744, 5,346,895, 5,346,915, 5,348,972, 5,348,975, 5,354,752 assigned to the assignee of the present application, describe or relate to compounds which include a chromanyl, thiochromanyl, or 1,2,3,4-tetrahydroquinolinyl moiety and have retinoid-like or related biological activity.

U.S. Pat. No. 5,344,959 describes cyclopropyl substituted 1,3-butadiene derivatives having retinoid-like biological activity.

Several co-pending applications and recently issued patents which are assigned to the assignee of the present application, are directed to further compounds having retinoid-like biological activity.

SUMMARY OF THE INVENTION

The present invention covers compounds of Formula

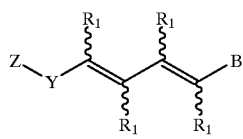

Formula 1 wherein Z is selected from the radicals shown in Formula 2 or in Formula 3,

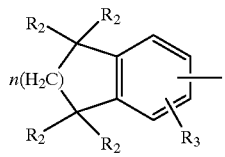

Formula 2

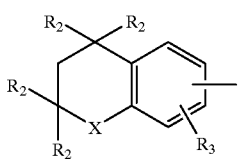

Formula 3

Y is cycloalkyl or cycloalkenyl of 3 to 8 carbons optionally substituted with one or two $R_4$ groups, or Y is selected from phenyl, pyridyl, thienyl, furyl, pyrrolyl, pyridazinyl, pyrimidinyl, pyrazinyl, thiazolyl, oxazolyl, and imidazolyl, said groups being optionally substituted with one or two $R_4$ groups, the divalent Y radical being substituted by the Z and $-CR_1=CR_1-CR=CR_1$ groups on adjacent carbons;

X is S, O, or $NR_5$;

n is 1 or 2;

$R_1$ and $R_2$ independently are H, lower alkyl or fluoroalkyl;

$R_3$ is hydrogen, lower alkyl, Cl or Br;

$R_4$ is lower alkyl, fluoroalkyl or halogen;

$R_5$ is H or lower alkyl, and

B is hydrogen, COOH or a pharmaceutically acceptable salt thereof, $COOR_8$, $CONR_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons, a cycloalkyl group of 5 to 10 carbons or trimethylsilylalkyl where the alkyl group has 1 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimerts disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

This invention also relates to a pharmaceutical formulation comprising a compound of Formula 1 in admixture with a pharmaceutically acceptable excipient.

In another aspect, this invention relates to processes for making a compound of Formula 1 which processes comprise reacting a compound of Formula 4 with a compound of Formula 5 in the presence of strong base, or reacting a compound of Formula 4 with a compound of Formula 6 in the presence of strong base. Alternatively, in the processes for making a compound of Formula 1, the aldehyde function of Formula 4 and the dialkylphosphonate of Formula 5, or the triphenylphosphonium bromide function of Formula 6, can be interchanged. In Formula 5 and Formula 6 the symbol B' represents B as defined above in connection with Formula 1, or such protected derivative of the group B from which the B group can be readily obtained by reactions well known to the practicing organic chemist. Still further, the present invention relates to such reactions performed on the compounds of Formula 1 which cause transformations of the B group while the reaction product still remains within the scope of Formula 1.

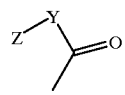

Formula 4

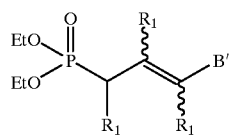

Formula 5

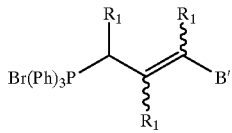

Formula 6

GENERAL EMBODIMENTS

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thioalcohols preferably with aliphatic alcohols having 1–6 carbons. Where the ester is derived from compounds where B is —$CH_2OH$, this term covers compounds derived from organic acids capable of forming esters including phosphorous based and sulfur based acids, or compounds of the formula —$CH_2OCOR_{11}$ where $R_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where X is (—OR)$_2$. Here, R is lower alkyl. Also, K may be —$OR_7O$— where $R_7$ is lower alkyl of 2–5 carbon atoms, straight chain or branched.

A pharmaceutically acceptable salt may be prepared for any compounds in this invention having a functionality capable of forming such-salt, for example an acid functionality. A pharmaceutically acceptable salt is any salt which retains the activity of the parent compound and does not impart any deleterious or untoward effect on the subject to which it is administered and in the context in which it is administered. Pharmaceutically acceptable salts may be derived from organic or inorganic bases. The salt may be a mono or polyvalent ion. Of particular interest are the inorganic ions, sodium, potassium, calcium, and magnesium. Organic salts may by be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well. In the present application when no specific mention is made of the configuration (cis, trans or R or S) of a compound (or of an asymmetric carbon) then a mixture of such isomers, or either one of the isomers is intended. In a similar vein, when in the chemical structural formulas of this application a straight line representing a valence bond is drawn to an asymmetric carbon, then isomers of both R and S configuration, as well as their mixtures are intended. A straight horizontal single line or a wavy single line drawn to a carbon with a double bond denotes either cis or trans or both orientations of the substituent on the double bond. Specific orientation of substituents relative to a double bond is indicated in the name of the respective compound, and/or by specifically showing in the structural formula the orientation of the substituents relative to the double bond.

With reference to the symbol Y in Formula 1, the preferred compounds of the invention are those where Y is cyclopropyl, phenyl, pyridyl, thienyl, or furyl. Even more preferred are compounds where Y is cyclopropyl or phenyl. In the preferred compounds of the invention there is no optional $R_4$ substituent on the Y group.

The $R_1$ substituent of the preferred compounds of the invention is preferably H or methyl. The B substituent of the preferred compounds is COOH or a pharmaceutically acceptable salt thereof, or $COOR_8$ or $CONR_9R_{10}$ where $R_8$, $R_9$ and $R_{10}$ are as defined above. Even more preferably $R_8$, $R_9$ and $R_{10}$ are lower alkyl.

Referring now to the radical symbolized by Z in Formula 1, it is preferably 5,6,7,8-tetrahydronaphthyl (Formula 2 where n is 2), chromanyl or thiochromanyl (Formula 3 where X is S or O). The Y group is preferably attached to the tetrahydronaphthalene group in the 2 or 3 position, and to the chroman or thiochroman ring in the 6 or 7 position. The $R_3$ substituent is preferably H or lower alkyl. Even more preferably the $R_3$ group is H or methyl, the Y group is attached to the tetrahydronaphthalene ring in the 2 position and to the chroman or thiochroman ring in the 6-position. The $R_2$ group is preferably H or methyl.

Specific preferred compounds in accordance with Formula 1 and their synthesis are described below in the section of this application titled "Specific Examples". The presently most preferred compounds of the invention in accordance with Formula 1 are indicated in Table 1 below, with reference to Formula 7, Formula 8 and Formula 9. The numbering of the pentadienoic acid chain of these compounds is indicated in Formula 7. In the preferred compounds of the invention the ▲$^4$ double bond is trans.

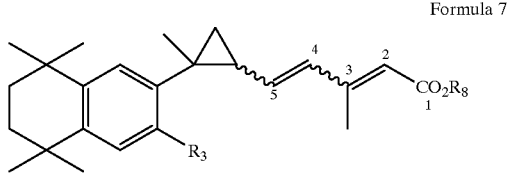

Formula 7

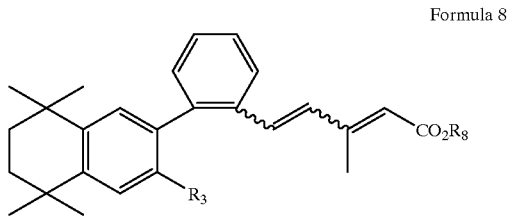

Formula 8

TABLE 1

![Formula 9 structure with CO2R6]

Formula 9

| Compound Number | Formula | X | $R_3$ | $R'_8$ | Configuration about cyclopropane | Configuration about $\blacktriangle^2$ bond | Configuration about $\blacktriangle^4$ bond |
|---|---|---|---|---|---|---|---|
| 1  | 7 | — | H | Et | cis | trans | trans |
| 2  | 7 | — | H | H  | cis | trans | trans |
| 3  | 7 | — | H | Et | trans | cis | trans |
| 4  | 7 | — | H | Et | trans | trans | trans |
| 5  | 7 | — | H | H  | trans | cis | trans |
| 6  | 7 | — | H | H  | trans | trans | trans |
| 7  | 8 | — | H | Et | — | trans | trans |
| 8  | 8 | — | H | Et | — | cis | trans |
| 9  | 8 | — | H | H  | — | trans | trans |
| 10 | 8 | — | H | H  | — | cis | trans |
| 11 | 7 | — | $CH_3$ | Et | cis | trans | trans |
| 12 | 7 | — | $CH_3$ | Et | cis | cis | trans |
| 13 | 7 | — | $CH_3$ | H | cis | trans | trans |
| 14 | 7 | — | $CH_3$ | H | cis | cis | trans |
| 15 | 9 | S | H | Et | cis | trans | trans |
| 16 | 9 | S | H | Et | cis | cis | trans |
| 17 | 9 | S | H | H  | cis | trans | trans |
| 18 | 9 | S | H | H  | cis | cis | trans |
| 19 | 9 | O | H | Et | cis | trans | trans |
| 20 | 9 | O | H | Et | cis | cis | trans |
| 21 | 9 | O | H | H  | cis | trans | trans |

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pennsylvania. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per mililiter of formulation will constitute a therapeutically effective concentration for total application. If administered systemically, an amount between 0.01 and 5 mg per kg per day of body weight would be expected to effect a therapeutic result in the treatment of many disease for which these compounds are useful.

Assay of Retinoid-like Biological Activity

The retinoid-like activity of the compounds of the invention can be confirmed in assays wherein ability of the compound to modulate processes mediated by retinoid receptors, and ability of the compounds to bind to retinoid receptors is measured. It is now general knowledge in the art that two main types of retinoic acid receptors exists in mammals (and other organisms). The two main types or families are respectively designated RAR and RXR receptors. Within each type there are sub-types, designated $RAR_\alpha$, $RAR_\beta$, $RAR_\gamma$, $RXR_\alpha$, $RXR_\beta$ and $RXR_\epsilon$. It has also been established in the art that the distribution of the two main retinoid receptor types, and of the several sub-types is not uniform in the various tissues and organs of mammalian organisms. Moreover, specific or selective agonist-like activity on RXR receptors, in preference over RAR receptors tends to result in certain beneficial retinoid-like properties while avoiding certain undesirable side effects. Similarly, selective agonist like activity of only one or two retinoid receptor subtypes within one retinoid receptor family can also give rise to beneficial pharmacological properties because of the varying distribution of the sub-types in the several mammalian tissues or organs. For the above-summarized reasons, agonist-like activity in any or all of the retinoid receptors, as well as specific or selective activity in the RXR receptor family, or selective or specific activity in any one of the receptor subtypes, are all considered desirable pharmacological properties.

In light of the foregoing the prior art has developed assay procedures for testing the agonist like activity of compounds in the $RAR_\alpha$, $RAR_\beta$, $RAR_\epsilon$, $RXR_\alpha$, $RXR_\beta$ and $RXR_\epsilon$ receptor subtypes. For example, a chimeric receptor trans-activation assay which tests for agonist-like activity in the $RAR_\alpha$, $RAR_\beta$, $RAR_\epsilon$, $RXR_\alpha$ receptor subtypes, and which is based on work published by Feigner P. L. and Holm M. (1989) Focus, 11 2 is described in detail in published PCT Application No. WO WO94/17796, published on Aug. 18, 1994. The latter publication is the PCT counterpart of U.S. application Ser. No. 08/016,404, filed on Feb. 11, 1993, in which a Notice of Allowance has been issued. PCT publication WO94/17796 and the specification of U.S. application Ser. No. 08/016,404 are hereby expressly incorporated by reference.

A holoreceptor transactivation assay and a ligand binding assay which measure the agonist like activity of the compounds of the invention, or their ability to bind to the several retinoid receptor sub-types, respectively, are described in published PCT Application No. WO WO93/11755 (particularly on pages 30–33 and 37–41) published on Jun. 24, 1993, the specification of which is also incorporated herein by reference. A description of the holoreceptor transactivation assay is also provided below.

HOLORECEPTOR TRANSACTIVATION ASSAY

CV1 cells (5,000 cells/well) were transfected with an RAR reporter plasmid ▲MTV-TREp-LUC (50 ng) along with one of the RAR expression vectors (10 ng) in an automated 96-well format by the calcium phosphate procedure of Heyman et al. Cell 68, 397–406. (8). For RXR transactivation assays, an RXR-responsive reporter plasmid CRBP II-TK-LUC (50 ng) along with one of the RXR expression vectors (10 ng) was used substantially as described by Heyman et al. above, and Allegretto et al. J. Biol. Chem. 268, 26625–26633. (8, 9). RXR-reporter contained DRI elements from human CRBP II promoter (see Mangelsdorf et al. The Retinoids: Biology, Chemistry and Medicine, pp 319–349, Raven Press Ltd., New York and Heyman et al., cited above) (1, 8). A β-galactosidase (50 ng) expression vector was used as an internal control in the transfections to normalize for variations in transfection efficiency. The cells were transfected in triplicate for 6 hours, followed by incubation with retinoids for 36 hours, and the extracts were assayed for luciferase and β-galactosidase activities. The detailed experimental procedure for holoreceptor transactivations has been described in Heyman et al. above, and Allegretto et al. cited above. The results obtained in this assay in connection with examplary compounds in accordance with the present invention are expressed in $EC_{50}$ numbers, as they are also in the chimeric receptor transactivation assay. The Heyman et al. Cell 68, 397–406, Allegretto et al. J. Biol. Chem. 268, 26625–26633, and Mangelsdorf et al. The Retinoids: Biology, Chemistry and Medicine, pp 319–349, Raven Press Ltd., New York, are expressly incorporated herein by reference. The results of ligand binding assay are expressed in $KD_{50}$ numbers.

Table 2 below shows the results of the holoreceptor transactivation assay and Table 3 discloses the efficacy (in percentage) in this assay of the compound relative to all trans retinoic acid, for certain exemplary compounds of the invention. Table 4 shows the results of the ligand binding assay for certain exemplary compounds of the invention.

TABLE 2

Holoreceptor Transactivation Assay $EC_{50}$ (nanomolar)

| Compound # | RARα | RARβ | RARΓ | RXRα | RXRβ | RXRΓ |
|---|---|---|---|---|---|---|
| 2 | 0.0 | 0.0 | 170 | 1.80 | 1.60 | 0.79 |
| 6 | 2100 | 340 | 200 | 2400 | 2300 | 2500 |
| 9 | 0.0 | 0.0 | 0.0 | 290 | 190 | 240 |
| 13 | 0.0 | 0.0 | 0.0 | 130 | 100 | 71.0 |
| 17 | 1200 | 48 | 270 | 30.0 | 19.0 | 13.0 |
| 21 | 0.0 | 1800 | 0.0 | 27.0 | 25.0 | 29.0 |

0.0 in Table 2 indicates a value greater than 1000 nM

TABLE 3

Transactivation Assay Afficacy (% of RA activity)

| Compound # | RARα | RARβ | RARΓ | RXRα | RXRβ | RXRΓ |
|---|---|---|---|---|---|---|
| 2 | 10.0 | 15.0 | 28.00 | 76.00 | 110.0 | 68.0 |
| 6 | 29.0 | 44.0 | 67.0 | 33.0 | 20.0 | 43.0 |
| 9 | 2.0 | 8.0 | 8.0 | 59.0 | 94.0 | 50.0 |
| 13 | 0.0 | 3.0 | 8.0 | 55.0 | 72.0 | 40.0 |
| 17 | 30 | 29 | 41 | 111 | 118 | 73 |
| 21 | 4.0 | 26.0 | 14.0 | 83.0 | 93.0 | 85.0 |

TABLE 4

Ligand Binding Assay $KD_{50}$ (nanomolar)

| Compound # | RARα | RARβ | RARΓ | RXRα | RXRβ | RXRΓ |
|---|---|---|---|---|---|---|
| 2 | 0.0 | 0.0 | 0.0 | 1.0 | 1.50 | 1.30 |
| 13 | 0.0 | 0.0 | 0.0 | 71.0 | 56.0 | 42.0 |
| 17 | 0.0 | 0.0 | 0.0 | 3.0 | 3.0 | 3.0 |
| 21 | 0.0 | 0.0 | 0.0 | 5.0 | 6.0 | 12.00 |

0.0 in Table 4 indicates a value greater than 1000 nM

SPECIFIC EMBODIMENTS

Synthetic Processes for Preparing Compounds of the Invention

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

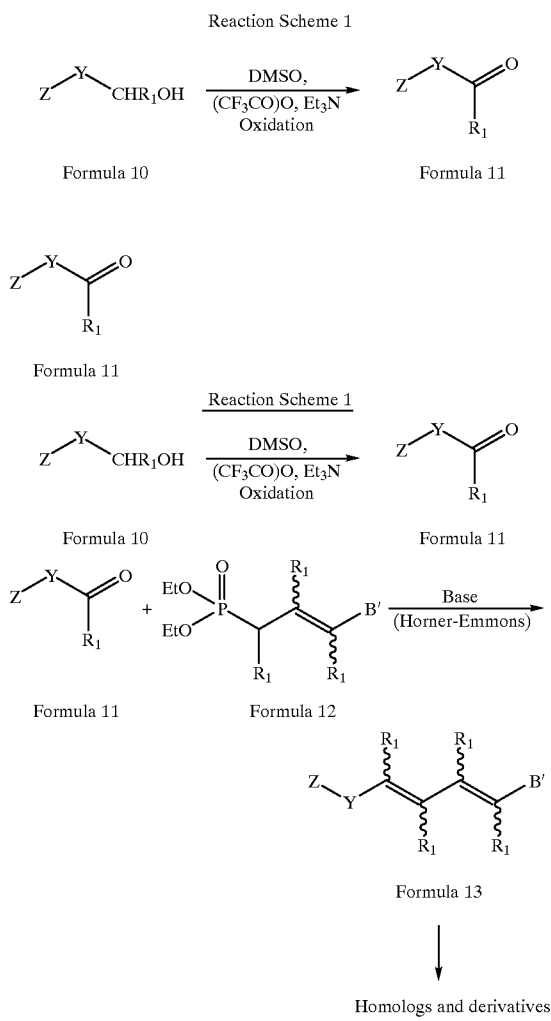

Referring now to Reaction Scheme 1 a primary or secondary alcohol of Formula 10 is the starting material. The symbols Z, Y and $R_1$ in this reaction scheme are defined as in connection with Formula 1. In the presently preferred embodiments the $R_1$ group of Formula 10 is hydrogen, and therefore the starting material is a primary alcohol. Examples of the primary alcohols which are used for the preparation of the preferred compounds of the present invention are 3-methyl-2(RS),3(SR)-methano-3[5,5,8,8-tetramethyl-5,6,7,8-tetrahydronaphth-2-yl]propan-1-ol, 3-methyl2(RS),3(RS)-methano-3[5,5,8,8-tetramethyl-5,6,7,8-tetrahydronaphth-2-yl]propan-1-ol, 2-(5,5,8,8-tetramethyl-5,6,7,8-tetrahydronaphth-2-yl)benzylalcohol, 3-methyl-2(RS),3(SR)-methano-3[4,4-dimethyl-thiochroman-6-yl]propan-1-ol, 3-methyl2(RS),3(SR)-methano-3[4,4-dimethyl-chroman -6-yl]propan-1-ol, 2-(4,4-dimethyl-thiochroman-6-yl) benzyl alcohol, 2-(4,4-dimethyl-chroman-6-yl)benzyl alcohol, 3-methyl-2(RS),3 (SR)-methano-3[4,4-dimethyl1,2,3,4-tetrahydroquinolin-6-yl]propan-1-ol and 2-(4,4-dimethyl-1,2,3,4-tetrahydroquinolin-6-yl)benzyl alcohol. Examples of the starting alcohol of Formula 10 for the preparations of compounds of the invention where Y is cyclopentyl or cyclohexyl are [2-(5,5,8,8-tetramethyl-5,6,7,8-tetrahydronaphth-2-yl)cyclopentyl]-methanol, [2-(5,5,8,8- tetramethyl-5,6,7,8-tetrahydronaphth-2-yl)-cyclohexyl]-methanol, (2-(4,4-dimethyl-thiochroman-6-yl)cyclopentyl]-methanol, 2-(4,4-dimethyl-thiochroman-6-yl)cyclohexyl]-methanol, 2-(4,4-dimethyl-chroman-6-yl)cyclopentyl]-methanol, 2-(4,4-dimethyl-chroman-6-yl)cyclohexyl)-methanol, [2-( 4,4-dimethyl-1,2,3,4-tetrahydroquinolin-6-yl)cyclopentyl]-methanol, 2-(4,4-dimethyl-1,2,3,4-tetrahydroquinolin-6-yl)cyclohexyl]-methanol.

The alcohol of Formula 10 is oxidized to provide the oxo compound of Formula 11. The oxidation can be carried out with a number of oxidizing agents known in the art; one suitable condition employed for the synthesis of the presently preferred embodiments is stirring the alcohol of Formula 10 with dimethylsulfoxide and trifluoroacetic anhydride. The oxo compound (aldehyde when $R_1$ is H) of Formula 11 is not necessarily isolated in an absolutely pure form, and can be used in a crude form in the next coupling reaction with the diethylphosphono reagent of Formula 12. The symbol $R_1$ in Formula 12 is defined as in connection with Formula 1; in the preferred embodiments $R_1$ of Formula 12 is H or methyl. The B' group of Formula 12 is defined as the B group of Formula 1, or such a protected derivative or precursor of B which can undergo and withstand the conditions of the Horner Emmons coupling reaction and from which the desired B group can be obtained by reactions well known to the practicing organic chemist. Typically, and preferably the B' group is an esterified carboxylic acid; an example of the reagent used for the preparation of the preferred compounds of the invention is ethyl diethylphosphono-3-methyl-2(E)-butenoate which can be obtained in accordance with the chemical literature (J. Org. Chem. 1974 Volume 39 p. 821). As is known in the art, the Horner Emmons reaction is conducted in the presence of strong base (such as butyl lithium) in an inert solvent (such as tetrahydrofuran) and results in the formation of a double bond to replace the oxo function of the reagent of Formula 11. The resulting product is a diene of Formula 13, wherein the B' group represents the B group of Formula 1 or a protected derivative thereof. In the preferred embodiments the B' or B group is a carboxylic acid or its ester, and therefore the presently preferred compounds of the invention are derivatives of 2,4-pentadienoic acid. Instead of the Horner Emmons reagent of Formula 12, an analogous Wittig reagent can also be utilized in the coupling reaction. The structure of such a Wittig reagent will be readily apparent to those skilled in the art in light of the present disclosure. The herein described Horner Emmons coupling reaction typically provides as predominant product the isomer where the configuration about the newly formed double bond ($\blacktriangle^4$ of the pentadienoic acid) is trans, and normally only this trans isomer is isolated from the reaction mixture. However, it is also possible to obtain a greater proportion of the corresponding cis isomer by adjusting conditions of the Horner Emmons reaction. As noted above, the B' group of the compounds of Formula 13 can be subjected to such reactions which are well within the skill of the practicing organic chemist, and which either result in the deprotection of B' to yield a B group within the scope of the invention, or which convert the B group into other functions still within the scope of the invention. Examples of the latter reactions are saponification, esterification, transesterification, amide formation, reduction to aldehyde and homologation. These reactions are indicated in Reaction Scheme 1 by conversion to "homologs and derivatives".

Reaction Scheme 2

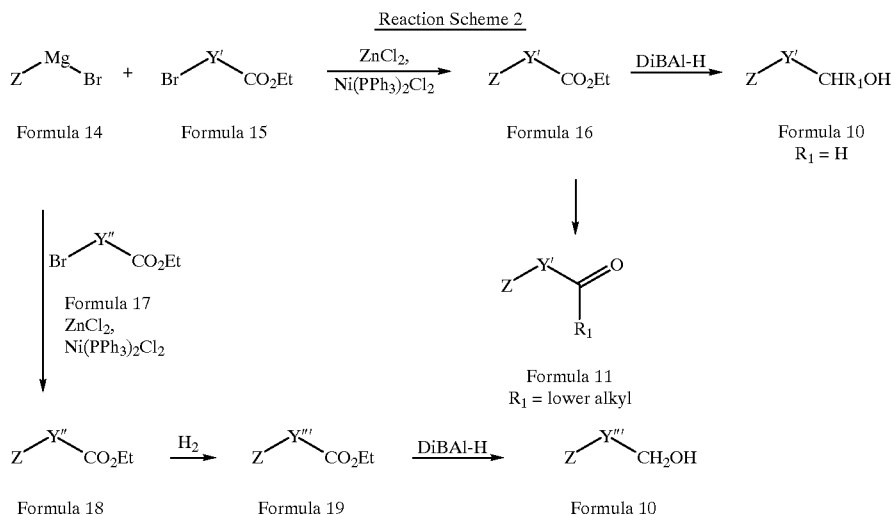

Referring now to Reaction Scheme 2, a general synthetic route is disclosed for obtaining the starting material used in the synthetic route described in Reaction Scheme 1 for the situation where in the formula of the compounds of the invention Y represents an aryl or heteroaryl group. Such group is symbolized by Y' in the reaction scheme. In accordance with this scheme, a Grignard or like organometallic reagent of Formula 14 is prepared from a compound of the formula Z-Br, and the Grignard reagent is reacted with bromo (or other halogeno) compound of Formula 15 in the presence of zinc chloride and triphenylphosphine nickel dichloride to obtain a carboxylate ester of Formula 16. The Z group is defined as above in connection with Formula 1.

An example of the reagent Z-Br utilized for the synthesis of certain preferred compounds of the invention is 2-bromo-5,5,8,8-tetramethyl-5,6,7,8-tetrahydronaphthalene (available in accordance with the chemical literature, see Journal of Medicinal Chemistry 1983 Vol. 26 p. 1653). Another example is 6- or 7-bromo-4,4-dimethylchroman, and 6- or 7-bromo-4,4-dimethylthiochroman which are available in accordance with the teachings of U.S. Pat. Nos. 5,348,972 and 5,053,523 the specifications of which is incorporated herein by reference.

In order for the modified Grignard coupling reaction between the reagents of Formula 14 and Formula 15 to proceed well, the bromo atom of the compound of Formula 15 must be attached to an aromatic (or heteroaromatic) carbon, or to a vinylic carbon. For this reason, the reagent of Formula 15 is a brominated (or other halogenated) arylcarboxylic acid ester, or bromo-heteroaryl carboxylic acid ester. These reagents are either commercially available, or generally speaking, can be prepared in accordance with the state of the art. An example for the reagent of Formula 15 which is used for the synthesis of certain preferred compounds of the invention is ethyl 2-bromobenzoate. Other examples for the reagent of Formula 15 are: ethyl 2-bromo-pyridine-3-carboxylate, ethyl 2-bromothiophene-3-carboxylate and ethyl 2-bromofuran-3-carboxylate.

The carboxylate ester product of Formula 16 is reduced with a suitable reducing agent, such as diisobutyl aluminum hydride (dibAlH) in an inert solvent such as methylene chloride, to yield the primary alcohol of Formula 10 where $R_1$ is hydrogen. The primary alcohol of Formula 10 is the starting material indicated in Reaction Scheme 1. The carboxylate ester compound of Formula 16 can also be converted to a ketone by a Grignard or modified Grignard reaction to yield the compounds of Formula 11 where the $R_1$ group is lower alkyl. The ketone compounds of Formula 11 can also serve in accordance with Reaction Scheme 1 for the synthesis of the compounds of the invention.

The synthetic methodology described above in connection with Reaction Scheme 2 is also suitable for preparation of compounds of the invention where the Y group is cycloalkyl, other than cyclopropyl. In such case, a brominated cycloalkenyl carboxylate ester of Formula 17 is reacted with the Grignard (or like organometallic) reagent of Formula 14 in the presence of zinc chloride and bis triphenyl phosphine nickel (II) chloride to provide compounds of Formula 18. Examples of reagents of Formula 17 are ethyl 2-bromocyclohexene carboxylate and ethyl 2-bromocyclopentene carboxylate. Accordingly, the Y" in Formula 17 represents a cycloalkene ring. Compounds of Formula 18 are subjected to hydrogenation to saturate the double bond in the cycloalkene ring, and thereafter reduced with diisobutyl aluminum hydride (dibAlH) to yield the primary alcohols of Formula 10. Y'" of Formula 19 of Reaction Scheme 2 represents a cycloalkyl ring. Compounds of Formula 17 can also be reduced to the alcohols of Formula 10 and follow Reaction Scheme 1 to provide cycloalkenyl compounds of the invention, as defined in Formula 1 where Y is cycloalkenyl.

Reaction Scheme 3
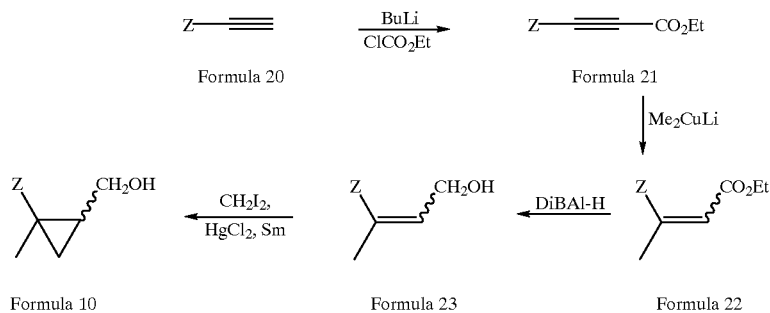
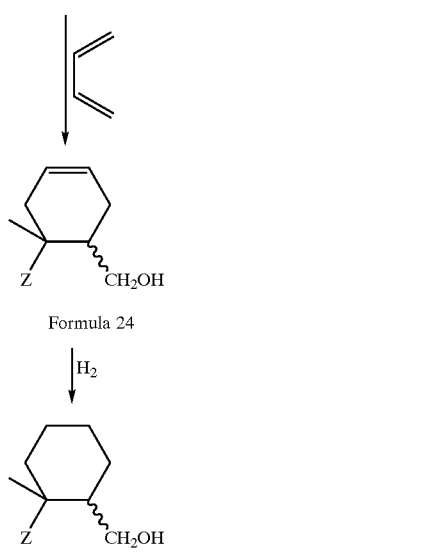
Reaction Scheme 3
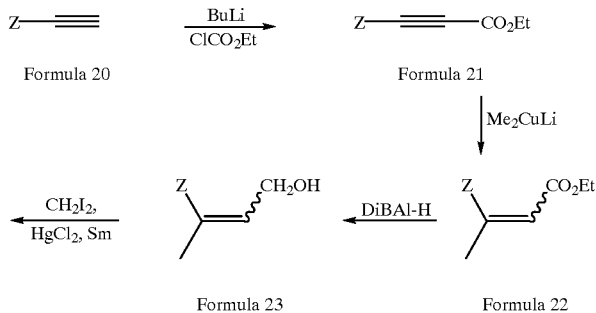
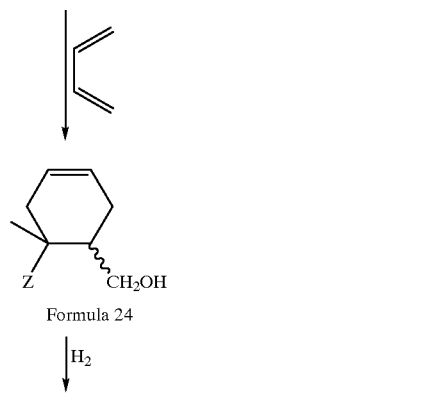

-continued

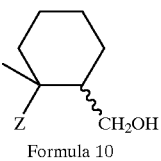
Formula 10

Reaction Scheme 3 discloses a synthetic route for the preparation of the starting primary alcohol (in accordance with Formula 10) for the synthesis of the preferred compounds of the invention where the Y group of Formula 1 is methylcyclopropyl. In accordance with this reaction scheme, an ethyne compound of the formula Z—C≡CH (Formula 20) is reacted with ethyl chloroformate (or methylchloroformate) in the presence of strong base (butyl lithium) in an inert solvent (such as hexane) to yield the propiolate compound of Formula 21. The ethyne compounds of Formula 20 are, generally speaking, known in the art. An examplary compound of Formula 20 which is used for the synthesis of the herein described preferred embodiments is 2-ethynyl-5,5,8,8-tetramethyl-5,6,7,8-tetrahydronaphthalene which can be obtained in accordance with the chemical literature, see The Retinoid: Biology, Chemistry and Medicine 2nd Edition, Editors Sporn et al., Raven Press Ltd. N.Y. 1994, Chapter 2, pg. 157. Further examples are (4,4-dimethyl-thiochroman-6-yl)ethyne, (4,4-dimethylchroman-6-yl)ethyne, (4,4-dimethyl-1,2,3,4-tetrahydroquinolin-6-yl)ethyne, (2,2,4,4-tetramethylthiochroman-6-yl)ethyne, (2,2,4,4-tetramethyl-chroman-6-yl)ethyne, (2,2,4,4-tetramethyl-1,2,3,4-tetrahydroquinolin-6-yl)ethyne, which can be obtained in accordance with the teachings of U.S. Pat. Nos. 5,053,523, 5,278,318, 5,346,895 and 5,348,972, the specifications of which is incorporated herein by reference. The propiolate compound of Formula 21 is thereafter reacted with methyl lithium in the presence of copper(I)bromide-dimethylsulfide in an inert solvent such as tetrahydrofuran. The reaction results in addition of the methyl group to the double bond, to yield the enoate compound of Formula 22. Depending on the reaction conditions which are described in detail below in the description of the specific embodiments, compounds of Formula 22 of both cis and trans orientation about the double bond can be obtained in this manner. The enoate compound of Formula 22 is thereafter reduced with a suitable reagent, such as diisobutyl aluminum hydride, to yield the primary alcohol of Formula 23. In the next step, the double bond of the alcohol of Formula 23 is converted into a cyclopropyl ring in a cyclopropylation reaction which employs the reagent diiodomethane in the presence mercury (II)chloride, and samarium. The cyclopropylation reaction is usually conducted at cold temperature (−78° C.), in an inert solvent such as tetrahydrofuran in an inert (argon) gas atmosphere. In the cyclopropylation reaction the orientation (cis or trans) of the double bond to which the methylene group is attached, is maintained, so that from a cis allylic alcohol of Formula 23 a cis cyclopropyl derivative is obtained, whereas a trans allylic alcohol of Formula 23 yields a trans cyclopropyl derivative. The product of the cyclopropylation reaction is the alcohol of Formula 10 (where Y is methylcyclopropyl) which is used as the starting compound for the synthesis of the compounds of the invention in accordance with Reaction Scheme 1. The unsaturated alcohol of Formula 23 (or preferably an ester thereof) can also be reacted with a diene compound (such as 1,3-butadiene) under Diels Alder conditions (heating in a sealed tube) to yield a cyclohexene derivative of Formula 24, which, after saturation of the double bond by hydrogenation, yields the alcohol of Formula 10, where Y is methyl cyclohexyl.

Referring now back to Reaction Scheme 1 and to the preparation of homologs and derivatives of the compounds of the invention, as well as to transformations of the B' group which may become necessary to obtain a desired reagent in accordance with Formula 12, where such reagent is not available commercially or from a known literature procedure, the following synthetic methodology is noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups,* Ed. Greene, John Wiley & Sons, 1981.

The acids and salts derived from compounds of Formula I are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with a 10-fold excess of oxalyl chloride. This is effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., Tet. Lett., 399, 1979), or dimethyl sulfoxide/ oxalyl chloride in methylene chloride (Omura, K., Swern, D., *Tetrahedron*. 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

SPECIFIC EMBODIMENTS

Ethyl 3-(5,5,8,8-tetramethyl-5,6,7,8-tetrahydronaphth-2-yl) propiolate (Compound A)

To a cold solution (−78° C.) of 2-ethynyl,5,5,8,8-tetramethyl-5,6,7,8-tetrahydronaphthalene (900 mgs, 4.3 mmols) in ether (20 ml) was added n-butyllithium in hexane (5.6 mmols). The mixture was stirred for 45 mins, and ethylchloroformate (1.3 g, 12 mmols) was added via syringe. Stirring was continued for 45 mins then the mixture was warmed gradually to −10° C. and quenched by adding sodium bicarbonate ($NaHCO_3$) solution (10 ml). Diethyl ether (100 ml) was added, the organic phase washed with water (10 ml), brine (10 ml), and dried ($MgSO_4$). The solvent was removed in vacuo. Purification of the residue over silicagel (5% ethylacetate in hexane) gave the title compound as a colorless oil.

PMR ($CDCl_3$) : δ1.27 (12H, s), 1.36 (3H, t, j=7.5 Hz), 1.68 (4H, s), 4.29 (2H, q, j=7.5 Hz), 7.30 (1H, d, j=8.2 Hz), 7.35 (1H, dd, j=1.6, 8.2 Hz), 7.56 (1H, d, j=1.6 Hz).

Ethyl 3-(5,5,8,8-tetramethyl-5,6,7,8-tetrahydronaphth-2-yl) but-2(Z)-enoate (Compound B)

To a cold (−20° C.) solution of copper(I)bromide-dimethylsulfide (CuBr.DMS) (832 mgs, 4.06 mmols) in THF (30 ml) methyllithium in ether (7.95 mmols) was added dropwise. The clear solution was stirred for 10 mins, then cooled to −78° C. To this solution ethyl 3-(5,6,7,8-tetrahydro-5,5,8,8-tetramethyl-naphth-2-yl)propiolate (Compound A, 900 mgs, 2.9 mmols) in THF (5 ml) was added dropwise (10 mins). The mixture was stirred for additional 2 hours at −78° C. The reaction was quenched by slow addition of ethanol to the cold (−78° C.) solution, followed by water (10 ml), and the mixture was diluted with more water (100 ml). The organic phase was washed with 10% HCl (10 ml), brine (10 ml) and dried (MgSO4). The solvent was removed in vacuo to give the title compound as a colorless oil. PMR ($CDCl_3$) : δ 1.03 (3H, t, j=7.5 Hz), 1.26 (6H, s), 1.28 (6H, s), 1.68 (4H, s), 2.17 (3H, d, j=1.4 Hz), 3.98 (2H, q, j=7.5 Hz), 5.86 (1H, q, j=1.4 Hz), 6.96 (1H, dd, j=2.0, 8.1 Hz), 7.14 (1H, d, j=2.0 Hz), 7.26 (1H, d, j=8.1 Hz).

3-(5,5,8,8-Tetramethyl-5,6,7,8-tetrahydronaphth-2-yl]but-2 (Z)-en-1-ol (Compound C)

To a cold (−78° C.) solution of ethyl 3-(5,5,8,8-tetramethyl-5,6,7,8-tetrahydronaphth-2-yl)but-2(Z) enoate (Compound B 500 mgs, 1.66 mmols) in THF (20 ml) was added DibAl-H in methylene chloride (6 mmols) dropwise (5 mins). The mixture was gradually (4 hours) allowed to warm to −10° C. The reaction was quenched by adding methanol (2 ml) followed by 10% HCl, and the mixture was stirred for 5 mins, then diethyl ether (100 ml) was added.

The organic phase was washed with water (10 ml), 10% $NaHCO_3$ (10 ml) and brine (10 ml) and dried ($MgSo_4$). The solvent was removed in vacuo to afford the title compound as a colorless oil.

PMR ($CDCl_3$): δ 1.28 (6H, s), 1.29 (6H, s), 1.69 (4H, s), 2.10 (3H, brs), 4.13 (2H, d, j=6.9 Hz), 5.69 (1H, t, j=6.9 Hz), 6.96 (1H, dd, j=2.1, 8.2 Hz), 7.09 (1H, d, j=2.1 Hz), 7.26 (1H, d, j=8.2 Hz).

3-Methyl-2 (RS),3(SR-methano-3(5,5,8,8-tetramethyl-5,6, 7,8-tetrahydronaphth-2-yl)propan-1-ol (Compound D)

To a flame dried round bottom flask containing samarium (1.125 g, 7.5 mmols) under argon atmosphere was added THF (10 ml), mercury(II)chloride (203 mgs, 0.75 mmol) in THF (10 ml) and 3-(5,5,8,8-tetramethyl-5,6,7,8,-tetrahydronaphth-2-yl)but-2(Z)-en-1-ol (Compound C 390 mgs, 1.5 mmols) in THF (5 ml), sequentially. The mixture was cooled to −78° C. and diiodomethane (2.01 g, 7.5 mmols) was added via syringe. The mixture was stirred and gradually warmed to ambient temperature (4h). The reaction was quenched by adding potassium carbonate solution (15 ml) and extracted with diethyl ether (5×25 ml). The organic phase was washed with water (10 ml), brine (10 ml) and dried ($MgSO_4$). The solvent was removed in vacuo, and purification of the residue by silicagel chromatography (5% ethylacetate in hexane) gave the title compound as a colorless oil. PMR ($CDCl_3$): δ 0.72–0.79 (1H, m), 0.83–0.91 (1H, m), 1.22–1.23 (1H, m) 1.26 (6H, s), 1.27 (6H, s), 1.40 (3H, s), 1.67 (4H, s), 3.12–3.22 (1H, m), 3.26–3.34 (1H, m), 7.06 (1H, dd, j=1.9, 8.1 Hz), 7.21 (1H, d, 8.1 Hz), 7.23 (1H, brs).

Ethyl 3.7-dimethyl,6(RS),7(SR) methano-7-(5,5,8,8-tetramethyl-5,6,7,8-tetrahydronaphth-2-yl),2(E),4(E)-heptadienoate (Compound 1)

To a cold (−70° C.) solution of dimethylsulfoxide (DMSO) (1.09 g, 14 mmols) in methylene chloride (10 ml) was added a solution of trifluoroacetic anhydride (2.52 g, 12 mmols) in methylene chloride (3 ml) dropwise (3 mins). To the stirred (10 mins) mixture was added a solution of 3-methyl-2(RS),3(SR)-methano-3(5,5,8,8-tetramethyl-5,6, 7,8-tetrahydronaphth-2-yl)propan-1-ol (Compound D, 598 mgs, 2.2 mmols) in methylene chloride (3 ml) dropwise. The mixture was stirred for additional 30 mins, then triethylamine (3.5 g, 35 mmols) in methylene chloride (5 ml) was added to it. The reaction mixture was allowed to warm to 0° C. (over 20 mins) and diluted with methylene chloride (60 ml). The organic phase was washed with water (10 ml), sodium bicarbonate (10 ml) and dried ($MgSO_4$). The solvent was removed in vacuo. Silicagel chromatography (5% ethyl acetate in hexane) of the crude product gave 3-methyl-2 (RS),3(SR)-methano-3(5,5,8,8-tetramethyl-5,6,7,8-tetrahydronaphth-2-yl)propionaldehyde. This unstable product was dissolved in dry THF (5 ml) and was added to a cold (−78° C.) solution of ethyl diethylphosphono-3-methyl-2 (E)-butenoate (792 mgs, 3 mmols) and n-butyllithium (2.88 mmols) in THF (10 ml). The mixture was stirred for 10 mins and quenched by adding water (10 ml) and diluted with diethyl ether (60 ml). The organic layer was washed with brine (10 ml) and dried ($MgSO_4$). The solvent was removed under reduced pressure. The crude product was purified by silicagel chromatography (3% ethylacetate in hexane) followed by HPLC (2% ethylacetate in hexane) to give the title compound as a colorless oil.

PMR ($CDCl_3$): δ 1.11–1.20 (2H, m),1.21 (3H, s), 1.28 (9H, s), 1.28 (3H, t, j=7.2 Hz), 1.43 (3H, s), 1.68 (4H, s), 1.68–1.80 (1H, m), 1.99 (3H, s), 4.15 (2H, q, j=7.2 Hz), 5.22 (1H, dd, j=9.9, 15.4 Hz), 5.63 (1H, s), 6.20 (1H, d, j=15.4 Hz), 7.03 (1H, dd, j=1.9, 8.1 Hz), 7.14 (1H, d, j=1.9 Hz), 7.23 (1H, d, j=8.1 Hz).

3,7-Dimethyl,6(RS),7(SR) methano-7-(5,5,8,8-tetramethyl-5,6,7,8-tetrahydronaphth-2-yl),2(E),4(E)-heptadienoic acid (Compound 2)

To a solution of ethyl 3,7-dimethyl,6(RS),7(SR) methano-7-(5,6,7,8-tetrahydro-5,5,8,8-tetramethylnaphth-2-yl),2(E),4(E)-heptadienoate (Compound 1 104 mgs, 027 mmols), in THF (2 ml) and methanol (1 ml) was added lithium hydroxide (1 mmol) in water, and the mixture was stirred at ambient temperature for 24 hours. Thereafter diethyl ether (60 ml) was added, the mixture was acidified with 10% HCl, and the organic phase was washed with water (5 ml), brine (5 ml), dried ($MgSO_4$) and the solvent was removed in vacuo. Chromatography on silicagel (25% ethylacetate in hexane) gave the title compound as a white solid.

PMR ($CDCl_3$): δ 1.12–1.22 (2H, m), 1.20 (3H, s), 1.27 (9H, s), 1.43 (3H, s), 1.67 (4H, s), 1.68–1.77 (1H, m), 1.98 (3H, s), 5.27 (1H, dd, j=9.9, 15.5 Hz), 5.65 (1H, s), 6.21 (1H, d, j=15.5 Hz), 7.03 (1H, dd, j=1.8, 8.0 Hz), 7.13 (1H, d, J=1.8 Hz), 7.23 (1H, d, J=8.0 Hz). Ethyl 3-(5,5,8,8-tetramethyl-5,6,7,8-tetrahydronaphth-2-yl)but-2(E)-enoate (Compound E)

Employing the same general procedure as for the preparation of ethyl 3-(5,5,8,8-tetramethyl-5,6,7,8-tetrahydronaphth-2-yl)but-2(Z)-enoate (Compound B), but instead using 900 gs (2.9 mmols) of ethyl 3-(5,5,8,8,-tetramethyl-5,6,7,8-tetrahydronaphth-2-yl)propiolate (Compound A), 832 mgs (4.06 mmols) of CuBr(I).DMS, 5.6 mmols of methyllithium in ether and -maintaining the temperature at 0° C. the title compound was obtained as a colorless oil.

PMR ($CDCl_3$): δ 1.29 (6H, s), 1.31 (6H, s), 1.33 (3H, t, j=7.1 Hz), 2.57 (3H, d, j=1.5 Hz), 4.22 (2H, q, j=7.1 Hz), 6.11 (1H, d, j=1.5 Hz), 7.25 (1H, dd, j=1.8, 8.3 Hz), 7.31 (1H, d, j=8.3 Hz), 7.41 (1H, d, j=1.8 Hz).

3-(5,5,8,8-Tetramethyl-5,6,7,8-tetrahydronaphth-2-yl) but-2(Z)-en-1-ol (Compound F)

Employing the same general procedure as used for the preparation of 3-(5,5,8,8-tetramethyl-5,6,7,8-tetrahydronaphth-2-yl)but-2(Z)-en-1-ol (Compound C), but instead using 500 mgs (1.66 mmols) of ethyl 3-(5,5,8,8-tetramethyl-5,6,7,8-tetrahydronaphth-2-yl) but-2(E)-enoate (Compound E) and 6 mmols of diisobutylaluminiumhydride the title compound was obtained as a colorless oil.

PMR ($CDCl_3$): δ 1.29 (6H, s), 1.30 (6H, s), 1.69 (4H, s), 2.08 (3H, s), 4.37 (12H, t, j=6.5 Hz), 5.90–5.99 (1H, m), 7.18 (1H, dd, j=1.8, 8.2 Hz), 7.27 (1H, d, j=8.2 Hz), 7.35 (1H, d, j=1.8 Hz).

(+/-)3-Methyl-2(RS),3(RS)-methano-3(5,5,8,8-tetramethyl-5,6,7,8-tetrahydronaphth-2-yl)propan-1-ol (Compound G)

Employing the same general procedure as used for the preparation of 3-methyl-2(RS),3(SR)-methano-3(5,6,7,8-tetrahydro-5,5,8,8-tetramethyl-naphth-2-yl)propan-1-ol (Compound D), but instead using 390 mgs (1.5 mmols) of 3-(5,6,7,8-tetrahydro-5,5,8,8-tetramethyl-naphth-2-yl)but-2(Z)-en-1-ol (Compound F), 1.125 g (7.5 mmols) of samarium, 203 mgs (0.75 mmol) of mercuric chloride and 2.01 g (7.5 mmols) of diiodomethane title compound was obtained as a colorless oil.

PMR ($CDCl_3$): δ 0.59 (1H, t, j=5.4 Hz), 1.12 (1H, dd, j=4.7, 8.9 Hz), 1.27 (6H, s), 1.29 (6H, s), 1.40–1.48 (1H, m), 1.46 (3H, s), 1.68 (4H, s), 3.65–3.78 (1H, m), 3.85–3.92 (1H, m), 7.02 (1H, dd, j=2.1, 8.2 Hz), 7.18 (1H, d, j=2.1 Hz), 7.23 (1H, d, j=8.2 Hz),

Ethyl 3,7-dimethyl,6(RS),7(RS) methano-7-(5,5,8,8-tetramethyl-5,6,7,8-tetrahydronaphth-2-yl),2(Z),4(E)-heptadienoate (Compound 3) and Ethyl 3.7-dimethyl,6(RS),7(RS) methano-7-(5,5,8,8-tetramethyl-5,6,7,8-tetrahydronaphth-2-yl),2(E),4(E)-heptadienoate (Compound 4)

Employing the same general procedure as used for the preparation of ethyl 3,7-dimethyl,6(RS),7(SR) methano-7-(5,6,7,8-tetrahydro-5,5,8,8-tetramethylnaphth-2-yl),2(E),4(E)-heptadienoate (Compound 1), but instead using 300 mgs (1.1 mmols) of 3-methyl-2(RS),3(RS)-methano-3[5,6,7,8-tetrahydro-5,5,8,8-tetramethyl-naphth-2-yl)propan-1-ol (Compound G), the starting compound was converted to the isomeric title compounds in the ratio of 4 (Compound 4): 1 (Compound 3).

Ethyl 3,7-dimethyl,6(RS),7(RS) methano-7-(5,5,8,8-tetramethyl-5,6,7,8-tetrahydronaphth-2-yl),2(Z),4(E)-heptadienoate (Compound 3)

PMR ($CDCl_3$): δ 0.96 (1H, t, j=5.2 Hz), 1.28 (6H, s), 1.29 (6H, s), 1.29 (3H, t, j=7.5 Hz), 1.45 (3H, s), 1.51 (1H, dd, j=4.9, 8.6 Hz), 1.68 (4H, s), 1.88–1.98 (1H, m), 2.03 (3H, s), 4.28 (2H, g, j=7.5 Hz), 5.59 (1H, s), 6.04 (1H, dd, j=9.0, 15.7 Hz), 7.01 (1H, dd, j=2.0, 8.2 Hz), 7.17 (1H, d, j=2.0 Hz), 7.23 (1H, d, j=8.2 Hz), 7.77 (1H d, j=15.7 Hz).

Ethyl 3,7-dimethyl,6(RS),7(RS) methano-7-(5,5,8,8-tetramethyl-5,6,7,8-tetrahydronaphth-2-yl),2(E),4(E) heptadienoate (Compound 4)

PMR ($CDCl_3$): δ 0.94 (1H, t, j=5.5 Hz), 1.27 (6H, s), 1.29 ((6H, s), 1.29 (3H, t, j=7.1 Hz), 1.45 (3H, s), 1.51 (1H, dd, j=4.9, 8.5 Hz), 1.68 (4H, s), 1.78–1.88 (1H, m), 2.31 (3H, s), 4.17 (2H, q, j=7.1 Hz), 5.72 (1H, s), 6.01 (1H, dd, j=9.0, 15.4 Hz), 6.28 (1H, d, j=15.4 Hz), 7.00 (1H, dd, j=2.1, 8.3 Hz), 7.17 (1H, d, j=2.1 Hz), 7.23 (1H, d, j=8.3 Hz).

3,7-Dimethyl,6(RS),7(RS) methano-7-(5,5,8,8-tetramethyl-5.6.7,8-tetrahydronaphth-2-yl),2(Z),4(E)-heptadienoic acid (Compound 5)

Employing the same general procedure as used for the preparation of 3,7-dimethyl,6(RS),7(SR) methano-7-(5,5,8,8-tetramethyl-5,6,7,8-tetrahydronaphth-2-yl),2(E),4(E)-heptadienoic acid (Compound 2), but instead using 30 mgs of ethyl 3,7-dimethyl,6(RS),7(RS) methano-7-(5,6,7,8-tetrahydro-5,5,8,8-tetramethylnaphth-2-yl),2(Z),4(E)-heptadienoate (Compound 3), and LiOH in water (1M solution, 1 ml), THF (2 ml), methanol (2 ml) the title compound was obtained as a white solid (21 mgs).

PMR ($CDCl_3$) : δ 0.98 (1H, t, j=5.5 Hz), 1.28 (6H, s), 1.29 (3H, s), 1.30 (3H, s), 1.46 (3H, s), 1.54 (1H, dd, j=4.9, 8.6 Hz), 1.68 (4H, s), 1.89–1.97 (1H, m), 2.06 (3H, s), 5.61 (1H, s), 6.09 (1H, dd, j=9.2, 15.7 Hz), 7.01 (1H, dd, J=2.1, 8.2 Hz), 7.17 (1H, d, j=2.1 Hz), 7.24 (1H, d, j=8.2 Hz), 7.74 (1H, d, j=15.7 Hz).

3,7-Dimethyl,6(RS),7(RS) methano-7-(5,5,8,8-tetramethyl-5,6,7,8-tetrahydronaphth-2-yl),2(E),4(E)-heptadienoic acid (Compound 6)

Employing the same general procedure used for the preparation of 3,7-dimethyl,6(RS),7(SR) methano-7(5,5,8,8-tetramethyl-5,6,7,8-tetrahydronaphth-2-yl),2(E),4(E)-heptadienoic acid (Compound 2), but instead using 100 mgs of ethyl 3,7-dimethyl,6(RS),7(RS) methano-7-(5,6,7,8-tetrahydro-5,5,8,8-tetramethylnaphth-2-yl),2(E),4(E)-heptadienoate (Compound 4), and LiOH in water (1M solution, 2 ml), THF (4 ml), methanol (2 ml) gave the title compound was obtained as a white solid.

PMR ($CDCl_3$): δ 0.95 (1H, t, j=5.4 Hz), 1.27 (6H, s), 1.28 (3H, s), 1.29 (3H, s), 1.45 (3H, s), 1.52 (1H, dd, j=5.0, 8.4 Hz), 1.68 (4H, s), 1.80–1.89 (1H, m), 5.74 (1H, s), 6.07 (1H, dd, j=9.2, 15.4 Hz), 6.32 (1H, d, j=15.4 Hz), 7.00 (1H, dd, j=2.0, 8.3 Hz), 7.16 (1H, d, j=2.0 Hz), 7.24 (1H, d, J=8.3 Hz).

Ethyl 2-[5,5,8,8-tetramethyl-5,6,7,8-tetrahydronaphth-2-yl] benzoate (Compound H)

To magnesium (180 mgs, 7.5 mmols) in THF (3 ml) was added a solution of 2-bromo-5,5,8,8-tetramethyl-5,6,7,8-tetrahydronaphthalene (200 mgs) in THF (5 ml) followed by 1,2-dibromoethane (94 mgs, 0.5 mmol). The mixture was stirred for 15 mins, then another portion of 2-bromo-5,5,8,8-tetramethyl-5,6,7,8-tetrahydronaphthalene (1.14 g, 5 mmols) in THF (10 ml) was added. The mixture was stirred for 15 mins at room temperature, and refluxed for 1 h. $ZnCl_2$ (680 mgs, 5 mmols) was added, stirred for 40 mins, and to the white precipitate. ethyl-2-bromobenzoate (1.09 g) in THF (5 ml) was added, immediately followed by addition of $Ni(PPh_2CH_2CH_2)Cl_2$ (26 mgs, 0.05 mmols). The mixture was stirred at room temperature for 16h. The reaction mixture was diluted with diethyl ether : ethylacetate (1:1, a total of 180 ml), the organic phase was washed with water (10 ml), brine (10 ml) $NaHCO_3$ (10 ml) and brine (10 ml), dried ($MgSO_4$) and the solvent was removed under reduced pressure. Silicagel chromatography (5% ethyl acetate in hexane) followed by HPLC purification of the crude material gave the title compound as a colorless oil. PMR ($CDCl_3$): δ 0.89 (3H, t, j=7.1 Hz), 1.29 (6H, s), 1.31 (6H, s), 4.04 (2H, q, j=7.1 Hz), 7.09 (1H, dd, j=2.0, 8.1 Hz), 7.22 (1H, d, j=2.0 Hz), 7.33 (1H, d, j=8.1 Hz), 7.40 (2H, d, j=6.9 Hz), 7.46–7.55 (1H, m), 7.76 (1H, d, j=7.1 Hz).

2-(5,5,8,8-Tetramethyl-5,6,7,8-tetrahydronaphth-2-yl) benzylalcohol (Compound I)

Employing the same general procedure as used for the preparation of 3-(5,5,8,8-tetramethyl-5,6,7,8-tetrahydronaphth-2-yl)but-2(Z)-en-1-ol (Compound C), but instead using 420 mgs (1.25 mmols) ethyl 2-[5,5,8,8-tetramethyl-5,6,7,8-tetrahydronaphth-2-yl]benzoate (Compound H) and 6 mmols of diisobutylaluminiumhydride the title compound was obtained as a white solid.

PMR ($CDCl_3$): δ 1.36 (6H, s), 1.39 (6H, S), 1.79 (4H, s), 4.67 (2H, s), 7.17 (1H, d, J=7.9 Hz), 7.34–7.44 (5H, m), 7.55–7.61 (1H, m).

Ethyl 3-methyl-5-[2-(5,5,8,8,-tetramethyl-5,6,7,8-tetrahydronaphth-2-yl)phenyl] pent-2(E),4(E)-dienoate (Compound 7) and Ethyl 3-methyl-5-[2-(5,5,8,8,-tetramethyl-5,6,7,8-tetrahydronaphth-2-yl)phenyl pent-2(Z),4(E)-dienoate (Compound 8)

Employing the same general procedure as used for the preparation of ethyl 3,7-dimethyl,6(RS),7(SR) methano-7-(5,5,8,8-tetramethyl-5,6,7,8-tetrahydronaphth-2-yl),2(E),4(E)-heptadienoate (Compound 2), but instead using 292 mgs (1 mmol) of 2-[5,5,8,8-tetramethyl-5,6,7,8-tetrahydronaphth-2-yl]benzylalcohol (Compound I), the starting material was converted to the isomeric title compounds in the ratio of 8 (Compound 7): 1 (Compound 8).

Compound 7:

PMR ($CDCl_3$): δ 1.25 (6H, s), 1.28 (3H, t, j=7.1 Hz), 1.32 (6H, s), 1.70 (4H, s), 2.22 (3H, brs), 4.16 (2H, q, j=7.1 Hz), 5.87 (1H, brs), 6.74 (1H, d, j=16.1 Hz), 7.01 (1H, d, j=16.1 Hz), 7.11 (1H, dd, j=1.8, 7.9 Hz), 7.22 (1H, d, j=1.8 Hz), 7.30–7.38 (4H, m), 7.59–7.69 (1H, m).

Compound 8:

PMR ($CDCl_3$): δ 1.29 (6H, s), 1.33 (3H, t, J=7.2 Hz), 1.35 (6H, s), 1.73 (4H, s), 1.96 (3H, s), 4.22 (2H, q, j=7.2 Hz), 5.71 (1H, s), 7.03 (1H, d, J=16.3 Hz), 7.15 (1H, dd, j=2.0, 8.1 Hz), 7.26 (1H, d, j=2.0 Hz), 7.32–7.39 (4H, m), 7.80–7.88 (1H, m), 8.39 (1H, d, j=16.3 Hz).

3-Methyl-5-[2-(5,5,8,8,-tetramethyl-5,6,7,8-tetrahydronaphth- 2-yl)phenyl] pent-2(E),4(E)-dienoic acid (Compound 9)

Employing the same general procedure used for the preparation of 3,7-dimethyl,6(RS),7(SR) methano-7-(5,5,8,8-tetramethyl-5,6,7,8-tetrahydronaphth-2-yl),2(E),4(E)-heptadienoic acid (Compound 2), but instead using 100 mgs of ethyl 3-methyl-5-[2-(5,5,8,8,-tetramethyl-5,6,7,8-tetrahydronaphth-2-yl)phenyl] pent-2(E),4(E)dienoate (7) and LiOH in water (1M solution, 1.5 ml), THF (2 ml), methanol (2 ml) the title compound was obtained as a white solid.

PMR ($CDCl_3$): δ 1.28 (6H, s), 1.35 (6H, s), 1.73 (4H, s), 2.26 (3H, s), 5.93 (1H, s), 6.79 (1H, d, J=16.1 Hz), 7.10 (1H, d, j=16.1 Hz), 7.14 (1H, dd, j=1.8, 8.2 Hz), 7.25 (1H, d, j=1.8 Hz), 7.34–7.41 (4H, m), 7.64–7.71 (1H, m).

3-Methyl-5-(2-(5,5,8,8,-tetramethyl-5,6,7,8-tetrahydronaphth-2-yl)phen-1-yl) pent-2(Z),4(E) -dienoic acid (Compound 10)

Employing the same general procedure as used for the preparation of 3,7-dimethyl,6(RS),7(SR) methano-7-(5,5,8,8-tetramethyl-5,6,7,8-tetrahydronaphth-2-yl),2(E),4(E)-heptadienoic acid (Compound 2), but instead using 20 mgs of ethyl 3-methyl-5-[2-(5,5,8,8,-tetramethyl-5,6,7,8-tetrahydronaphth-2-yl)phenyl] pent-2(Z),4(E)dienoate (Compound 8) and LiOH in water (1M solution, 0.5 ml), THF (2 ml), methanol (2 ml) the title compound was obtained as a white solid.

PMR ($CDCl_3$): δ 1.30 (6H, s), 1.35 (6H, s), 1.74 (4H, s), 2.00 (3H, s), 5.75 (1H, s), 7.09 (1H, d, j=15.9 Hz), 7.15 (1H, dd, j=1.7, 8.2 Hz), 7.32–7.41 (4H, m), 7.78–7.83 (1H, m), 8.32 (1H, d, j=15.9 Hz).

Ethyl 3-[3,5,5,8,8,-pentamethyl-5,6,7,8-tetrahydronaphth-2-yl]propiolate (Compound J)

Employing the same general procedure as used for the preparation of ethyl 3-[5,5,8,8,-tetramethyl-5,6,7,8-tetrahydronaphth-2-yl]propiolate (Compound A), but instead using 1.9 g of (3-methyl-5,5,8,8,-tetramethyl-5,6,7,8-tetrahydronaphth-2-yl)ethyne, 940 mgs (10 mmols) of methylchloroformate and 8.8 mmols of n-butyllithium the title compound was obtained as an oil.

PMR ($CDCl_3$): δ 1.26 (6H, s), 1.27 (6H, s), 1.67 (4H, s), 2.43 (3H, s), 3.85 (3H, s), 7.16 (1H, s), 7.51 (1H, s) .

Methyl 3-[3,5,5,8,8-pentamethyl-5,6,7,8-tetrahydronaphth-2-yl]but-2(Z)-enoate (Compound K)

Employing the same general procedure as for the preparation of ethyl 3-(5,5,8,8-tetramethyl-5,6,7,8-tetrahydronaphth-2-yl]but-2(Z)-enoate (Compound B), but instead using 2.05 gs (6.4 mmols) of methyl 3-[3,5,5,8,8,-pentamethyl-5,6,7,8-tetrahydronaphth-2-yl)propiolate (Compound J), 2.1 gs (10.24 mmols) of CuBr.DMS, 18 mmols of methyl lithium in diethyl ether and maintaining the temperature at −78° C. the title compound was obtained as a white solid.

PR ($CDCl_3$): δ 1.24 (6H, s), 1.28 (6H, s), 1.67 (6H, s), 2.12 (3H, s), 2.15 (3H, s), 3.50 (3H, s), 5.96 (1H, s), 6.86 (1H, s), 7.08 (1H, s).

3-[3,5,5,8,8-Pentamethyl-5,6,7,8-tetrahydronaphth-2-yl] but-2(Z)-en-1-ol (Compound L)

Employing the same general procedure as used for the preparation of 3-(5,5,8,8-tetramethyl-5,6,7,8-tetrahydronaphth-2-yl)but-2(Z)-en-1-ol (Compound C), but instead using 1.85 gs (6.1 mmols) of methyl 3-(3,5,5,8,8-pentamethyl-5,6,7,8-tetrahydronaphth-2-yl]but-2(Z)-enoate (compound K) and 15 mmols of diisobutylaluminiumhydride the title compound was obtained as a white solid.

PMR ($CDCl_3$): δ 1.25 (6H, s), 1.28 (6H, s), 1.67 (4H, s), 2.00 (3H, s), 2.16 (3H, s), 3.84 (2H, d, J=7.1 Hz), 5.73 (1H, dt, j=1.6, 7.1 Hz), 6.90 (1H, s), 7.08 (1H, s).

3-Methyl-2(RS),3(SR)-methano-3[3,5,5,8,8-pentamethyl-5,6,7,8-tetrahydronaphth-2-yl]propan-1-ol (Compound X)

Employing the same general procedure as used for the preparation of 3-methyl-2(RS),3(SR)-methano-3[5,5,8,8- tetramethyl-5,6,7,8-tetrahydronaphth-2-yl]propan-1-ol (Compound D), instead using 1.1 gs (4 mmols) of 3-[3,5,5,8,8-pentamethyl-5,6,7,8-tetrahydronaphth-2-yl]but-2(Z)-en-1-ol (Compound L), 3.1 g (20.6 mmols) of samarium, 450 mgs (1.7 mmol) of mercuric chloride and 5.8 g (21.6 mmols) of diiodomethane the title compound was obtained as a colorless oil. PMR ($CD_3COCD_3$): δ 0.60 (1H, brs), 0.80 (1H, brs), 1.23 (9H,s), 1.24 (3H, s), 1.64 (4H, s), 1.63–1.67 (1H, m), 2.33 (3H, s), 2.85 (3H, s), 3.34–3.48 (2H, m), 7.06 (1H, s), 7.25 (1H, brs).

Ethyl 3,7-dimethyl,6(RS),7(SR) methano-7-(3,5,5,8,8-pentamethyl-5,6,7,8-tetrahydronaphth-2-yl),2(E),4(E)-heptadienoate (Compound 11) and Ethyl 3,7-dimethyl,6(RS),7(SR) methano-7-(3,5,5,8,8-pentamethyl-5,6,7,8-tetrahydronaphth-2-yl),2(Z),4(E)-heptadienoate (Compound 12)

Employing the same general procedure as used for the preparation of ethyl 3,7-dimethyl,6(RS),7(SR) methano-7-(5,5,8,8-tetramethyl-5,6,7,8-tetrahydronaphth-2-yl),2(E),4(E)-heptadienoate (Compound 2), but instead using 390 mgs (1.4 mmols) of 3-methyl-2(RS),3(RS)-methano-3[3,5,5,8,8-pentamethyl-5,6,7,8-tetrahydronaphth-2-yl]propan-1-ol (Compound M), the starting material was converted to the isomeric title compounds in the ratio of 8 (Compound 11): 1 (Compound 12).

Compound 11:
PMR ($CDCl_3$): δ 0.96 (1H, brs), 1.20 (1H, brs), 1.25 (3H, s), 1.26 (3H, s), 1.27 (6H, s), 1.29 (3H, t, j=7.1 Hz), 1.37 (3H, s), 1.66 (4H, s), 1.70–1.80 (1H m), 2.04 (3H, brs), 2.31 (3H, brs), 4.16 (2H, g, j=7.1 Hz), 5.30 (1H, brs), 5.66 (1H, brs), 6.25 (1H, d, j=15.5 Hz), 7.04 (1H, s), 7.07 (1H, brs).

Compound 12:
PMR ($CDCl_3$): δ 0.95 (1H, brs), 1.19 (1H, brs), 1.23 (3H, s), 1.25 (9H, s), 1.30 (3H, t, J=7.1 Hz), 1.35 (3H, s), 1.64 (4H, s), 1.71 (3H, brs), 1.80–1.90 (1H, m), 2.31 (3H, BRS), 4.17 (2H, q, j=7.1 Hz), 5.31 (1H, brs), 5.49 (1H, s), 7.02 (1H, s), 7.08 (1H, brs), 7.78 (1H, d, J=15.6 Hz).

3.7-Dimethyl,6(RS),7(SR) methano-7-(3,5,5,8,8-pentamethyl-5,6,7,8-tetrahydronaphth-2-yl),2(E),4(E)-heptadienoic acid (Compound 13)

Employing the same general procedure as used for the preparation of 3,7-dimethyl,6(RS),7(SR) methano-7-(5,5,8,8-tetramethyl-5,6,7,8-tetrahydronaphth-2-yl),2(E),4(E)-heptadienoic acid (Compound 2), but instead using 100 mgs of ethyl 3,7-dimethyl,6(RS),7(RS) methano-7-(3,5,5,8,8-pentamethyl-5,6,7,8-tetrahydronaphth-2-yl),2(E),4(E)-heptadienoate (Compound 4) and LiOH in water (1M solution, 1 ml), THF (4 ml), methanol (2 ml) the title compound was obtained as a white solid.

PMR ($CD_3COCD_3$): δ 1.01 (1H, brs), 1.18 (1H, s), 1.21 (3H, s), 1.23 (3H, s), 1.24 (6H, s), 1.33 (3H, s), 1.64 (4H, s), 1.70–1.86 (1H, m), 1.97 (3H, brs), 2.29 (3H, brs), 5.31 (1H, brs), 5.68 (1H, s), 6.31 (1H, d, j=15.8 Hz), 7.09 (2H, s).

3,7-Dimethyl,6(RS),7(SR) methano-7-(3,5,5,8,8-pentamethyl-5,6,7,8-tetrahydronaphth-2-yl),2(Z),4(E)-heptadienoic acid (Compound 14)

Employing the same general procedure as used for the preparation of 3,7-dimethyl,6(RS),7(SR) methano-7-(5,5,8,8-tetramethyl-5,6,7,8-tetrahydronaphth-2-yl),2(E),4(E)-heptadienoic acid (Compound 2), but instead using 12 mgs of ethyl 3,7-dimethyl,6(RS),7(RS) methano-7-(3,5,5,8,8-pentamethyl-5,6,7,8-tetrahydronaphth-2-yl),2(Z),4(E)-heptadienoate (Compound 12) and LiOH in water (1M solution in water 0.4 ml) the title compound was obtained as a white solid.

PMR ($CDCl_3$): δ 1.01 (1H, brs), 1.20 (1H, s), 1.24 (12H, s), 1.35 (3H, s), 1.66 (4H, s), 1.79–1.89 (1H, m), 2.30 (3H, brs) 2.83 (3H, brs), 5.30 (1H,brs), 5.52 (1H, s), 7.10 (2H, brs), 7.81 (1H, d, j=16.4 Hz).

Methyl 3-(4,4-dimethyl-thiochroman-6-yl propiolate (Compound N)

Employing the same general procedure as used for the preparation of ethyl 3-(5,5,8,8,-tetramethyl-5,6,7,8-tetrahydronaphth-2-yl)propiolate (Compound A), but instead using 2.0 g (10 mmols) of (4,4-dimethylthiochroman-6-yl)ethyne, 2 g (21.3 mmols) of methylchloroformate and 11 mmols of n-butyl lithium the title compound was obtained as a yellow solid.

PMR ($CDCl_3$): δ 1.31 (6H, s), 1.90–1–1.97 (2H, m), 3.00–3.07 (2H, m), 3.83 (3H, s), 7.07 (1H, d, J=8.1 Hz), 7.22 (1H, dd, j=1.8, 8.1 Hz), 7.57 (1H, d, j=1.8 Hz).

Methyl 3-[4,4-dimethyl-thiochroman-6-yl] but-2(Z)-enoate (Compound O)

Employing the same general procedure as for the preparation of ethyl 3-[5,5,8,8-tetramethyl-5,6,7,8-tetrahydronaphth-2-yl]but-2(Z)-enoate (Compound B), but instead using 1.6 g (6.1 mmols) of methyl 3-[4,4-dimethyl-thiochroman-6-yl]propiolate (Compound N), 2.1 g (10.24 mmols) of CuBr.DMS, 18 mmols of methyl lithium in ether and maintaining the temperature at −78° C., the title compound was obtained as a colorless oil.

PMR ($CDCl_3$): δ 1.33 (6H, s), 1.97 (2H, t, j=6.0 Hz), 3.03 (2H, t, j=6.0 Hz), 3.58 (3H, s), 5.87 (1H, s), 6.93 (1H, dd, j=1.9, 8.1 Hz), 7.05 (1H, d, j=8.1 Hz), 7.24 (1H, d, j=1.9 Hz).

3-[4,4-Dimethyl-thiochroman-6-yl]but-2(Z)-en-1-ol (Compound P)

Employing the same general procedure used for the preparation of 3-[5,5,8,8-tetramethyl-5,6,7,8-tetrahydronaphth-2-yl]but-2(Z)-en-1-ol (Compound C), but instead using 1.3 g (4.7 mmols) of methyl 3-[4,4-dimethyl-thiochroman-6-yl]but-2(Z)-enoate (Compound O) and 15 mmols of diisobutylaluminiumhydride the title compound was obtained as a colorless oil.

PMR ($CDCl_3$): δ 1.34 (6H, s), 1.95–2.00 (2H, m), 2.08 (3H, s), 3.01–3.05 (2H, m), 4.10 (2H, d, j=7.0 Hz), 5.67 (1H, d, j=7.0 Hz), 6.87 (1H, dd, j=2.0, 8.1 Hz), 7.05 (1H, d, j=8.1 Hz), 7.17 (1H, d, j=2.0 Hz).

3-Methyl-2(RS),3(SR)-methano-3[4,4-dimethyl-thiochroman-6-yl]propan-1-ol (Compound O)

Employing the same general procedure as used for the preparation of 3-methyl-2(RS), 3(SR)-methano-3[5,5,8,8-tetramethyl-5,6,7,8-tetrahydronaphth-2-yl]propan-1-ol (Compound D), but instead using 1.23 g (4.5 mmols) of 3-[4,4-dimethyl-thiochroman-6-yl] but-2(Z)-en-1-ol (Compound P), 3.95 g (26.3 mmols) of samarium, 520 mgs (1.92 mmols) of mercuric chloride and 6.95 g (25.9 mmols) of diiodomethane the title compound was obtained as a colorless oil.

PMR ($CDCl_3$): δ 0.75–0.85 (2H, m), 1.20–1.31 (1H, m), 1.32 (6H, s), 1.96 (2H, t, j=5.9 Hz), 3.01 (2H, t, j=5.9 Hz), 3.15–3.29 (2H, m), 7.00 (2H, s), 7.31 (1H, s).

Ethyl 3,7-dimethyl,6(RS),7(SR) methano-7-[4,4-dimethylthiochroman-6-yl),2(E),4(E)-heptadienoate (Compound 15) and Ethyl 3,7-dimethyl,6(RS),7(SR) methano-7-(4,4-dimethyl-thiochroman-6-yl),2(Z),4(E)-heptadienoate (Compound 16)

Employing the same general procedure as used for the preparation of ethyl 3,7-dimethyl,6(RS),7(SR) methano-7-(5,5,8,8-tetramethyl-5,6,7,8-tetrahydronaphth-2-yl),2(E),4(E)-heptadienoate (Compound 2), but instead using 245 mgs (0.95 mmol) of 3-methyl-2(RS),3(RS)-methano-3[4,4-dimethyl-thiochroman-6-yl]propan-1-ol (Compound Q), the starting material was converted to the isomeric title compounds in the ratio of 4 (Compound 15): 1 (Compound 16).

Compound 15:

PMR (CDCl$_3$): δ 1.09 (1H, t, j=5.1 Hz), 1.17 (1H, dd, j=5.7, 8.2 Hz), 1.25 (3H, s), 1.27 (3H, t, j=7.1 Hz), 1.32 (3H, s), 1.39 (3H, s), 1.67–1.76 (1H, m), 1.92–1.98 (2H, m), 2.01 (3H, s), 2.98–3.04 (2H, m), 4.14 (2H, q, J=7.1 Hz), 5.22 (1H, dd, j=10.0, 15.5 Hz), 5.64 (1H, s), 6.20 (1H, d, j=15.5 Hz), 6.95 (1H, dd, j=1.8, 8.1 Hz), 7.01 (1H, d, j=8.1 Hz), 7.20 (1H, d, j=1.8 Hz).

Compound 16:

PMR (CD$_3$COCD$_3$): δ 1.17–1.22 (2H, m), 1.22 (3H, t, j=7.1 Hz), 1.26 (3H, s), 1.30 (3H, s), 1.40 (3H, s), 1.67 (3H, s), 1.77–1.86 (1H, m), 1.90–1.96 (2H, m), 2.97–3.03 (2H, m), 4.09 (2H, q, j=7.1 Hz), 5.27 (1H, dd, j=9.9, 15.9 Hz), 5.47 (1H, s), 6.95 (1H, d, j=8.2 Hz), 6.98 (1H, dd, j=1.7, 8.2 Hz), 7.74 (1H, d, j=15.9 Hz).

3,7-Dimethyl,6(RS),7(SR) methano-7-(4,4-dimethylthiochroman-6-yl),2(E),4(E-heptadienoic acid (Compound 17)

Employing the same general procedure as used for the preparation of 3,7-dimethyl,6(RS),7(SR) methano-7-(5,5,8,8-tetramethyl-5,6,7,8-tetrahydronaphth-2-yl),2(E),4(E)-heptadienoic acid (Compound 2), but instead using 100 mgs (0.28 mmol) of ethyl 3,7-dimethyl,6(RS),7(RS) methano-7-(4,4-dimethylthiochroman-6-yl),2(E),4(E)-heptadienoate (Compound 15) and LiOH in water (1M solution in water, 0.4 ml) the title compound was obtained as a white solid.

PMR (CDCl$_3$): δ 1.10 (1H, t, j=4.9 Hz), 1.19 (1H, dd, j=4.9, 8.2 Hz), 1.25 (3H, s), 1.32 (3H, s), 1.4 (3H, s), 1.69–1.79 (1H, m), 1.95 (2H, t, j=6.5 Hz), 2.01 (3H, s), 3.01 (2H, t, j=6.5 Hz), 5.27 (1H, dd, j=10.0, 15.5 Hz), 5.66 (1H, s), 6.24 (1H, d, J=15.5 Hz), 6.95 (1H, dd, j=1.8, 8.1 Hz), 7.01 (1H, d, j=8.1 Hz), 7.20 (1H, dd, j=1.8 Hz).

3,7-Dimethyl,6(RS),7 (SR) methano-7-(4,4-dimethylthiochroman- 6-yl),2(Z),4(E-heptadienoic acid (Compound 18)

Employing the same general procedure as used for the preparation of 3,7-dimethyl,6(RS),7(SR) methano-7-(5,5,8,8-tetramethyl-5,6,7,8-tetrahydronaphth-2-yl),2(E),4(E)-heptadienoic acid (Compound 2), but instead using 30 mgs (0.08 mmol) of ethyl 3,7-dimethyl,6(RS),7(RS) methano-7-(4,4-dimethyl-thiochroman-6-yl),2(Z),4(E)-heptadienoate (16) and LiOH in water (1M solution in water 0.5 ml) the title compound was obtained as a white solid.

PMR (CDCl$_3$): δ 1.12 (1H, t, j=4.9 Hz), 1.22 (1H, dd, j=4.9, 8.1 Hz), 1.28 (3H, s), 1.34 (3H, s), 1.41 (3H, s), 1.75 (3H, s), 1.82–1.92 (1H, m), 1.95–2.01 (2H, m), 3.03 (2H, t, j=5.9 Hz), 5.28 (1H, dd, j=10.1, 15.7 Hz), 5.54 (1H, s), 6.97 (1H, dd,j=1.8, 8.0 Hz),7.03 (1H, d, j=8.0 Hz), 7.24 (1H, d, j=1.8 Hz), 7.73 (1H, d, t=15.7 Hz.

Methyl 3-(4,4-dimethyl-chroman-6-yl)propiolate (Compound R)

Employing the same general procedure as used for the preparation of ethyl 3-[5,5,8,8,-tetramethyl-5,6,7,8-tetrahydro-naphth-2-yl]propiolate (Compound A) but instead using 1.86 g (10 mmols) of [4,4-dimethylchroman-6-yl]ethyne, 2 g (21.3 mmols) of methylchloroformate and 11 mmols of n-butyllithium the title compound was obtained as a yellow solid.

PMR (CDCl$_3$): δ 1.32 (6H, s), 1.82 (2H, t, j=5.6 Hz, 3.82 (3H, s), 4.22 (2H, t, j=5.6 Hz), 6.75 (1H, d, j=8.6 Hz), 7.30 (1H, dd, j=2.0, 8.6 Hz), 7.53 (1H, d, 2.0 Hz).

Methyl 3-[4,4-dimethyl-chroman-6-yl]but-2(Z-enoate (Compound S)

Employing the same general procedure as for the preparation of ethyl 3-[5,5,8,8-tetramethyl-5,6,7,8-tetrahydro-naphth-2-yl]but-2(Z)-enoate (Compound B) but instead using 1.4 g (5.7 mmols) of methyl 3-(4,4-dimethyl-chroman-6-yl]propiolate (Compound R), 2.1 g (10.24 mmols) of CuBr.DMS, 18 mmols of methyllithium in ether and maintaining the temperature at −78° C. the title compound was obtained as a colorless oil.

PMR (CDCl$_3$): δ 1.34 (6H, s), 1.85 (2H, t, j=5.4 Hz), 2.18 (3H, s), 3.58 (3H, s), 4.20 (2H, t, j=5.4 Hz), 5.85 (1H, s), 6.76 (1H, d, k=8.5 Hz), 7.00 (1H, dd, j=2.2 Hz, 8.5 Hz).

3-[4,4-Dimethyl-chroman-6-yl]but-2 (Z)-en-1-ol (Compound T)

Employing the same general procedure used for the preparation of 3-(5,5,8,8-tetramethyl-5,6,7,8-tetrahydro-naphth-2-yl but-2(Z)-en-1-ol (Compound C) but instead using 270 mgs (1.04 mmols) of methyl 3-[4,4-dimethyl-chroman-6-yl]but-2(Z)-enoate (Compound S) and 4 mmols of diisobutylaluminiumhydride the title compound was obtained as a colorless oil.

PMR (CDCl$_3$): δ 1.34 (6H, s), 1.85 (2H, t, j=5.4 Hz), 2.08 (3H, s), 4.12 (2H, d, j=6.2 Hz), 4.20 (2H, d, j=5.4 Hz), 5.67 (1H, t, j=6.2 Hz), 6.75 (1H, d, j=8.3 Hz), 6.92 (1H, dd, j=2.1, 8.3 Hz), 7.08 (1H, d, j=2.1 Hz).

3-Methyl-2(RS),3(SR)-methano-3[4,4-dimethyl-chroman-6-yl]propan-1-ol (Compound U)

Employing the same general procedure as used for the preparation of 3-methyl-2(RS),3(SR)-methano-3[5,5,8-8-tetramethyl-5,6,7,8-tetrahydro-naphth-2-yl]propan-1-ol (Compound D) but instead using 230 mgs (1 mmol) of 3-[4,4-dimethyl-chroman-6-yl] but-2(Z)-en-1-ol (Compound T) 750 mgs (5 mmols) of samarium, 130 mgs (0.5 mmol) of mercuricchloride and 1.35 g (5 mmols) of diiodomethane the title compound was obtained as a colorless oil.

PMR (CDCl$_3$): δ 0.74–0.83 (2H, m), 1.22–1.27 (1H, m), 1.33 (3H, s), 1.37 (3H, s), 1.83 (2H, t, j=5.4 Hz), 3.12–3.34 (2H, m), 4.17 (2H, d, j=5.4 Hz), 6.72 (1H, d, j=8.3 Hz), 7.02 (1H, dd, j=2.2, 8.3 Hz), 7.21 (1H, d, j=2.2 Hz).

Ethyl 3,7-dimethyl,6(RS),7(SR) methano-7-(4,4-dimethylchroman-6-yl),2(E),4(E)-heptadieonate (Compound 19) and ethyl 3,7-dimethyl,6(RS),7(SR) methano-7-(4,4-dimethylchroman-6-yl),2(Z),4(E)-heptadienoate (Compound 20)

Employing the same general procedure as used for the preparation of ethyl 3,7-dimethyl,6(RS),7(SR) methano-7(5,5,8,8-tetramethyl-5,6,7,8-tetrahydronaphth-2-yl),2(E),4(E)-heptadienoate (Compound 1) but instead using 110 mgs (0.5 mmol) of 3-methyl-2(RS),3(RS)-methano-3[4,4-dimethyl-chroman-6-yl]propan-1-ol (compound U) isomeric title compounds were obtained in the ratio of 4 (Compound 19): 1 (Compound 20)

compound 19:

PMR (CDCl$_3$): δ 1.07 (1H, t, j=4.7 Hz), 1.15 (1H, dd, j=4.7, 8.2 Hz), 1.26 (3H,), 1.26 (3H, t, j=7.1 Hz), 1.31 (3H, s), 1.38 (3H, s), 1.65–1.74 (1H, m), 1.81 (2H, t, j=5.4 Hz), 1.99 (3H, s), 4.13 (2H, q, j=7.1 Hz), 4.17 (2H, t, j=5.4 Hz), 5.22 (1H, dd, j=9.9, 15.6 Hz), 5.63 (1H, s), 6.19 (1H, d, j=15.6 Hz), 6.70 (1H, d, j=8.3 Hz), 6.96 (1H, dd, j=2.2, 8.3 Hz), 7.10 (1H, d, j=2.2 Hz).

Compound 20:

PMR (CDCl$_3$): δ 1.07 (1H, t, j=4.7 Hz), 1.17 (1H, dd, j=4.7, 8.2 Hz), 1.25 (3H, s), 1.29 (3H, t, j=7.1 Hz), 1.31 (3H, s), 1.37 (3H, s), 1.68 (3H, brs), 1.75–1.85 (3H, m), 4.12–4.21 (4H, m), 5.21 (1H, dd, j=8.9, 15.8 Hz), 5.47 (1H, s), 6.70 (1H, d, j=8.3 Hz), 6.97 (1H, dd, j=2.2, 8.3 Hz), 7.11 (1H, d, j=2.2 Hz), 7.72 (1H, d, j=15.8 Hz).

3,7-Dimethyl,6(RS),7(SR) methano-7-[4,4-dimethylchroman-6-yl),2(E),4(E)-heptadienoic acid (Compound 21)

Employing the same general procedure used for the preparation of 3,7-dimethyl,6(RS),7(SR) methano-7-(5,5,8, 8-tetramethyl-5,6,7,8-tetrahydro-naphth-2-yl),2(E),4(E)-heptadienoic acid (Compound 2) but instead using 21 mgs (0.06 mmol) of ethyl 3,7-dimethyl,6(RS),7(RS) methano-7-(4,4-dimethyl-chroman-6-yl),2(E),4(E)-heptadienoate (Compound 19) and LiOH in water (1M solution in water 0.4 ml) gave the title compound as a white solid.

PMR (CDCl$_3$): δ 1.10 (1H, t, j=4.9 Hz), 1.18 (1H, dd, j=4.9, 8.1 Hz), 1.26 (3H, s), 1.32 (3H, s), 1.40 (3H, s), 1.67–1.79 (1H, m), 1.82 (2H, t, j=5.8 Hz), 2.00 (3H, s), 4.17 (2H, t, j=5.8 Hz), 5.28 (1H, dd, j=9.9, 15.4 Hz), 5.65 (1H, s), 6.22 (1H, d, j=15.4 Hz), 6.72 (1H, d, j=8.3 Hz), 6.97 (1H, dd, j=2.1 Hz, 8.3 Hz), 7.10 (1H, d, j=2.1 Hz).

What is claimed is:

1. A compound of Formula 1

Formula 1 wherein Z is the group shown in Formula 3,

Formula 3

Y is cyclopropyl, said Y group being optionally substituted with one or two R$_4$ groups, the divalent Y radical being substituted by the Z and —(CR$_1$=CR$_1$—CR$_1$=CR$_1$)— groups on adjacent carbons;

X is NR$_5$;

R$_1$ and R$_2$ independently are H, lower alkyl or fluoroalkyl;

R$_3$ is hydrogen, lower alkyl, Cl or Br;

R$_4$ is lower alkyl, fluoroalkyl or halogen;

R$_5$ is H or lower alkyl, and

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or tri-lower alkylsilyl, where R$_7$ is an alkyl of 1 to 5 carbons; cycloalkyl of 3 to 5 carbons or alkenyl group containing 2 to 5 carbons, R$_8$ is an alkyl group of 1 to 10 carbons, a cycloalkyl group of 5 to 10 carbons or trimethylsilylalkyl where the alkyl group has 1 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons.

2. A compound of the formula wherein X is NR$_5$;

R$_5$ is H or lower alkyl;

R$_2$ is H or lower alkyl;

R$_3$ is H or lower alkyl, and

B is hydrogen, COOH or a pharmaceutically acceptable salt thereof, COOR$_8$, CONR$_9$R$_{10}$, —CH$_2$OH, CH$_2$OC$_{11}$, CH$_2$OCOR$_{11}$, CHO, CH(OR$_{12}$)$_2$, CHOR$_{13}$, —COR$_7$, CR$_7$(OR$_{12}$)$_2$, CR$_7$OR$_{13}$O, or tri-lower alkylsilyl, where R$_7$ is an alkyl of 1 to 5 carbons, cycloalkyl of 3 to 5 carbons or alkenyl group containing 2 to 5 carbons, R$_8$ is an alkyl group of 1 to 10 carbons, a cycloalkyl group of 5 to 10 carbons or trimethylsilylalkyl where the alkyl group has 1 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons.

3. A compound in accordance with claim 2 wherein R$_2$ is methyl.

4. A compound in accordance with claim 3 wherein B is COOH or a pharmaceutically acceptable salt thereof, COOR$_8$ or CONR$_9$R$_{10}$.

5. A compound in accordance with claim 4 where the cyclopropyl group is attached to the 7 position of the tetrahydroquinoline nucleus.

6. A compound in accordance with claim 5 where the configuration about the ▲$^4$ double bond is trans.

7. A compound in accordance with claim 5 where B is COOH.

8. A compound in accordance with claim 5 where B is COOC$_2$H$_5$.

9. A compound in accordance with claim 1 where the cyclopropyl group is attached to the 7 position of the tetrahydroquinoline nucleus.

* * * * *

UNITED STATES PATENT AND TRADEMARK OFFICE
CERTIFICATE OF CORRECTION

PATENT NO. : 6,034,242
DATED : March 7, 2000
INVENTOR(S) : Vuligonda et al.

Page 1 of 3

It is certified that error appears in the above-identified patent and that said Letters Patent is hereby corrected as shown below:

Title Page ABSTRACT:
Line 10 nelow Formula 3, "$CO_9R_{10}$" should be --$CONR_9R_{10}$--.

Column 1:
Line 5, insert --1.-- before "CROSS-REFERENCE".
Line 15, insert --2.-- before "FIELD".
Line 34, insert --3.-- before "BACKGROUND".

Column 3:
Line 35, $CONR_{10}$" should be --$CONR_9R_{10}$--.

Column 4:
Line 12, "Alzheimerts" should be --Alzheimer's--.
Line 45, Formula 4, " 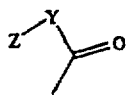 " should be -- 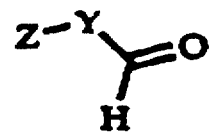 --

Column 5:
Line 51, "x" should be --K--.
Line 65, delete "by".

Column 7:
Line 20, "TABLE 1" should be under Formula 9.
Line 23, Formula 9, "$R_6$" should be --$R_8$--.

Column 8:
Line 56, "$RXR_e$" should be --$RXR_\gamma$--.

Column 9:
Line 9, "$RAR_e$" should be --$RAR_\gamma$--; "$RXR_e$" should be --$RXR_\gamma$--.
Line 12, "$RAR_e$" should be --$RAR_\gamma$--.
Line 56, "examplary" should be --exemplary--.

Column 10:
Line 23, "Afficacy" should be --Efficacy--.

UNITED STATES PATENT AND TRADEMARK OFFICE
CERTIFICATE OF CORRECTION

PATENT NO.   : 6,034,242
DATED        : March 7, 2000
INVENTOR(S)  : Vuligonda et al.

Page 2 of 3

It is certified that error appears in the above-identified patent and that said Letters Patent is hereby corrected as shown below:

Column 11:
Lines 1-15, delete

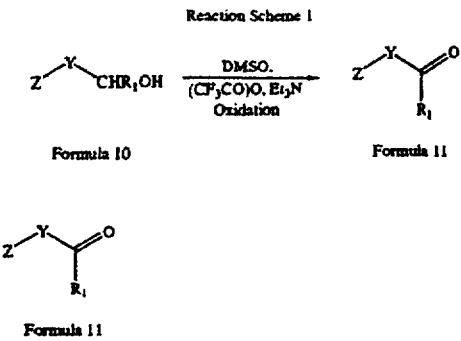

Line 55, after "methyl", insert -- - --.

Columns 15-17, delete the second occurrence of Reaction Scheme 3.

Column 17:
Line 21, "examplary" should be --exemplary".

Column 18:
Line 36, "I" should be --1--.

Column 19:
Line 31, "MgSO4" should be --MgSO$_4$--.
Line 52, "MgSO4" should be --MgSO$_4$--.

Column 20:
Line 2, "MgSo$_4$" should be --MgSO$_4$--.

Column 21:
Line 19, "Ethyl" should start a new line.
Line 28, "-maintaining" should be --maintainig--.

Column 22:
Line 20, after "4.28 (2H, ", "g" should be --q--.

UNITED STATES PATENT AND TRADEMARK OFFICE
CERTIFICATE OF CORRECTION

PATENT NO. : 6,034,242
DATED : March 7, 2000
INVENTOR(S) : Vuligonda et al.

It is certified that error appears in the above-identified patent and that said Letters Patent is hereby corrected as shown below:

Column 23:
Line 35, "(6H,S)" should be --(6H,s)--.

Column 24:
Line 65, "x" should be --m--.

Column 25:
Line 30, after "4.16 (2H,", "g" should be --q--.

Column 27:
Line 17, after "4(E", insert --)--.
Line 34, after "4(E", insert --)--.
Line 49, after "15.7 Hz", insert --)--.
Line 59, after "5.6 Hz", insert --)--.
Line 62, after "2(z", insert --)_--.

Column 28:
Line 7, "k=8.5 Hz" should be --j=8.5 Hz--.

Column 30:
Line 23, "$CHOR_{13}$" should be --$CHOR_{13}O$--.

Signed and Sealed this

Thirty-one Day of July, 2001

*Attest:*

NICHOLAS P. GODICI
*Attesting Officer*    *Acting Director of the United States Patent and Trademark Office*